United States Patent
Gerber et al.

(10) Patent No.: US 7,563,286 B2
(45) Date of Patent: Jul. 21, 2009

(54) CONTROLLED ARTIFICIAL INTERVERTEBRAL DISC IMPLANT

(75) Inventors: David Gerber, West Chester, PA (US); Justin K. Coppes, West Chester, PA (US); Christopher Angelucci, Schwenksville, PA (US); David C. Paul, Phoenixville, PA (US); Pascal Stihl, West Chester, PA (US); Michael L. Boyer, Paoli, PA (US)

(73) Assignee: Synthes USA, LLC, West Chester, PA (US)

( * ) Notice: Subject to any disclaimer, the term of this patent is extended or adjusted under 35 U.S.C. 154(b) by 807 days.

(21) Appl. No.: 11/056,010

(22) Filed: Feb. 11, 2005
(Under 37 CFR 1.47)

(65) Prior Publication Data
US 2005/0251260 A1  Nov. 10, 2005

Related U.S. Application Data

(63) Continuation of application No. PCT/US03/25536, filed on Aug. 15, 2003.

(60) Provisional application No. 60/403,356, filed on Aug. 15, 2002, provisional application No. 60/403,402, filed on Aug. 15, 2002.

(51) Int. Cl.
*A61F 2/44* (2006.01)
(52) U.S. Cl. .................................. 623/17.14; 623/17.15
(58) Field of Classification Search .... 623/17.11–17.16

See application file for complete search history.

(56) References Cited

U.S. PATENT DOCUMENTS

| 3,867,728 A | 2/1975 | Stubstad et al. |
| 3,875,595 A | 4/1975 | Froning |
| 3,958,278 A | 5/1976 | Lee et al. |
| 4,309,777 A | 1/1982 | Patil |
| 4,349,921 A | 9/1982 | Kuntz |
| 4,759,766 A | 7/1988 | Buettner-Janz et al. |
| 4,759,769 A | 7/1988 | Hedman et al. |

(Continued)

FOREIGN PATENT DOCUMENTS

DE  28 04 936  8/1979

(Continued)

OTHER PUBLICATIONS

International Search Report from PCT/US2003/25536.

*Primary Examiner*—Bruce E Snow
(74) *Attorney, Agent, or Firm*—Stroock & Stroock & Lavan LLP

(57) ABSTRACT

The invention relates to an artificial intervertebral disc for placement between adjacent vertebrae. The artificial intervertebral disc is preferably designed to restore disc height and natural disc curvature, allow for a natural range of motion, absorb shock and provide resistance to motion and axial compression. Furthermore, the intervertebral disc may be used in the cervical, the thoracic, or the lumbar regions of the spine. The artificial intervertebral disc may include either singularly or in combination: an interior including at least one spring member preferably incorporating a arcuate surface member, a flexible core, the flexible core preferably being a slotted core, a ring spring, a winged leaf spring, or a leaf spring, or The articulating member preferably being attached to one of the endplate by an intermediate shock absorbing element.

40 Claims, 12 Drawing Sheets

U.S. PATENT DOCUMENTS

| | | | |
|---|---|---|---|
| 4,772,287 A | 9/1988 | Ray et al. | |
| 4,863,477 A | 9/1989 | Monson | |
| 4,904,260 A | 2/1990 | Ray et al. | |
| 4,911,718 A | 3/1990 | Lee et al. | |
| 4,932,969 A | 6/1990 | Frey et al. | |
| 4,932,975 A | 6/1990 | Main et al. | |
| 4,946,378 A | 8/1990 | Hirayama et al. | |
| 4,963,152 A | 10/1990 | Hofmann et al. | |
| 5,002,576 A | 3/1991 | Fuhrmann et al. | |
| 5,071,437 A | 12/1991 | Steffee | |
| 5,108,442 A | 4/1992 | Smith | |
| 5,123,926 A | 6/1992 | Pisharodi | |
| 5,171,280 A | 12/1992 | Baumgartner | |
| 5,171,281 A | 12/1992 | Parsons et al. | |
| 5,192,327 A | 3/1993 | Brantigan | |
| 5,236,460 A | 8/1993 | Barber | |
| 5,246,458 A | 9/1993 | Graham | |
| 5,258,031 A | 11/1993 | Salib et al. | |
| 5,306,307 A | 4/1994 | Senter et al. | |
| 5,314,477 A | 5/1994 | Marnay | |
| 5,320,644 A | 6/1994 | Baumgartner | |
| 5,360,430 A | 11/1994 | Lin | |
| 5,370,697 A | 12/1994 | Baumgartner | |
| 5,401,269 A | 3/1995 | Buttner-Janz et al. | |
| 5,423,816 A | 6/1995 | Lin | |
| 5,425,773 A | 6/1995 | Boyd et al. | |
| 5,458,642 A | 10/1995 | Beer et al. | |
| 5,458,643 A | 10/1995 | Oka et al. | |
| 5,507,816 A | 4/1996 | Bullivant | |
| 5,514,180 A | 5/1996 | Heggeness et al. | |
| 5,534,029 A | 7/1996 | Shima | |
| 5,534,030 A | 7/1996 | Navarro et al. | |
| 5,554,191 A | 9/1996 | Lahille et al. | |
| 5,562,736 A | 10/1996 | Ray et al. | |
| 5,593,445 A | 1/1997 | Waits | |
| 5,674,294 A | 10/1997 | Bainville et al. | |
| 5,674,296 A | 10/1997 | Bryan et al. | |
| 5,676,701 A | 10/1997 | Yuan et al. | |
| 5,676,702 A | 10/1997 | Ratron | |
| 5,683,465 A | 11/1997 | Shinn et al. | |
| 5,702,450 A | 12/1997 | Bisserie | |
| 5,755,796 A | 5/1998 | Ibo et al. | |
| 5,776,202 A | 7/1998 | Copf et al. | |
| 5,782,832 A | 7/1998 | Larsen et al. | |
| 5,827,328 A | 10/1998 | Buttermann | |
| 5,888,223 A | 3/1999 | Bray, Jr. | |
| 5,888,226 A | 3/1999 | Rogozinski | |
| 5,893,889 A * | 4/1999 | Harrington | 623/17.16 |
| 5,895,428 A | 4/1999 | Berry | |
| 5,899,941 A | 5/1999 | Nishijima et al. | |
| 5,928,284 A | 7/1999 | Mehdizadeh | |
| 5,989,291 A | 11/1999 | Ralph et al. | |
| 6,019,792 A | 2/2000 | Cauthen | |
| 6,039,763 A | 3/2000 | Shelokov | |
| 6,045,579 A | 4/2000 | Hochshuler et al. | |
| 6,063,121 A | 5/2000 | Xavier et al. | |
| 6,080,193 A | 6/2000 | Hochshuler et al. | |
| 6,093,205 A | 7/2000 | McLeod et al. | |
| 6,113,637 A | 9/2000 | Gill et al. | |
| 6,113,639 A | 9/2000 | Ray et al. | |
| 6,132,465 A | 10/2000 | Ray et al. | |
| 6,136,031 A | 10/2000 | Middleton | |
| 6,139,579 A | 10/2000 | Steffee et al. | |
| 6,143,031 A | 11/2000 | Knothe et al. | |
| 6,146,421 A | 11/2000 | Gordon et al. | |
| 6,146,422 A | 11/2000 | Lawson | |
| 6,162,252 A | 12/2000 | Kuras et al. | |
| 6,176,882 B1 | 1/2001 | Biedermann et al. | |
| 6,179,874 B1 | 1/2001 | Cauthen | |
| 6,187,043 B1 | 2/2001 | Ledergerber | |
| 6,193,757 B1 | 2/2001 | Foley et al. | |
| 6,228,118 B1 | 5/2001 | Gordon | |
| 6,231,609 B1 | 5/2001 | Mehdizadeh | |
| 6,283,998 B1 | 9/2001 | Eaton | |
| 6,296,664 B1 | 10/2001 | Middleton | |
| 6,296,665 B1 | 10/2001 | Strnad et al. | |
| 6,315,797 B1 | 11/2001 | Middleton | |
| 6,332,894 B1 | 12/2001 | Stalcup et al. | |
| 6,368,350 B1 | 4/2002 | Erickson et al. | |
| 6,375,681 B1 | 4/2002 | Truscott | |
| 6,375,682 B1 | 4/2002 | Fleischmann et al. | |
| 6,375,683 B1 | 4/2002 | Crozet et al. | |
| 6,383,221 B1 | 5/2002 | Scarborough et al. | |
| 6,395,030 B1 | 5/2002 | Songer et al. | |
| 6,395,031 B1 | 5/2002 | Foley et al. | |
| 6,395,032 B1 | 5/2002 | Gauchet | |
| 6,402,784 B1 | 6/2002 | Wardlaw | |
| 6,402,785 B1 | 6/2002 | Zdeblick et al. | |
| 6,413,278 B1 | 7/2002 | Marchosky | |
| 6,416,551 B1 | 7/2002 | Keller | |
| 6,419,704 B1 | 7/2002 | Ferree | |
| 6,419,705 B1 | 7/2002 | Erickson | |
| 6,419,706 B1 | 7/2002 | Graf | |
| 6,425,920 B1 | 7/2002 | Hamada | |
| 6,440,168 B1 | 8/2002 | Cauthen | |
| 6,440,169 B1 | 8/2002 | Elberg et al. | |
| 6,454,806 B1 | 9/2002 | Cohen et al. | |
| 6,468,310 B1 | 10/2002 | Ralph et al. | |
| 6,478,801 B1 | 11/2002 | Ralph et al. | |
| 6,482,234 B1 | 11/2002 | Weber et al. | |
| 6,517,580 B1 | 2/2003 | Ramadan et al. | |
| 6,527,804 B1 | 3/2003 | Gauchet et al. | |
| 6,579,320 B1 | 6/2003 | Gauchet et al. | |
| 6,582,466 B1 | 6/2003 | Gauchet | |
| 6,582,468 B1 | 6/2003 | Gauchet | |
| 6,626,943 B2 | 9/2003 | Eberlein et al. | |
| 6,645,248 B2 | 11/2003 | Casutt | |
| 6,656,178 B1 | 12/2003 | Veldhuizen et al. | |
| 6,682,562 B2 | 1/2004 | Viart et al. | |
| 6,712,853 B2 | 3/2004 | Kuslich | |
| 6,733,532 B1 | 5/2004 | Gauchet et al. | |
| 6,733,533 B1 | 5/2004 | Lozier | |
| 6,770,095 B2 | 8/2004 | Grinberg et al. | |
| 6,881,228 B2 | 4/2005 | Zdeblick et al. | |
| 6,893,465 B2 | 5/2005 | Huang | |
| 6,899,735 B2 | 5/2005 | Coates et al. | |
| 6,936,071 B1 | 8/2005 | Marnay et al. | |
| 6,958,077 B2 | 10/2005 | Suddaby | |
| 6,966,929 B2 | 11/2005 | Mitchell | |
| 6,966,931 B2 | 11/2005 | Huang | |
| 6,969,405 B2 | 11/2005 | Suddaby | |
| 6,984,246 B2 | 1/2006 | Huang | |
| 6,986,789 B2 | 1/2006 | Schultz et al. | |
| 6,994,727 B2 | 2/2006 | Khandkar et al. | |
| 7,001,431 B2 | 2/2006 | Bao et al. | |
| 7,048,766 B2 | 5/2006 | Ferree | |
| 7,056,345 B2 | 6/2006 | Kuslich | |
| 7,060,100 B2 | 6/2006 | Ferree et al. | |
| 7,077,865 B2 | 7/2006 | Bao et al. | |
| 7,105,024 B2 | 9/2006 | Richelsoph | |
| 7,118,580 B1 | 10/2006 | Beyersdorff et al. | |
| 7,147,665 B1 | 12/2006 | Bryan et al. | |
| 7,153,325 B2 | 12/2006 | Kim et al. | |
| 7,156,877 B2 | 1/2007 | Lotz et al. | |
| 7,166,130 B2 | 1/2007 | Ferree | |
| 7,179,294 B2 | 2/2007 | Eisermann et al. | |
| 7,198,644 B2 | 4/2007 | Schultz et al. | |
| 7,204,852 B2 | 4/2007 | Marnay et al. | |
| 7,214,243 B2 | 5/2007 | Taylor | |
| 7,235,101 B2 | 6/2007 | Berry et al. | |
| 2001/0032017 A1 | 10/2001 | Alfaro et al. | |
| 2002/0029082 A1 | 3/2002 | Muhanna et al. | |
| 2002/0035400 A1 | 3/2002 | Bryan et al. | |
| 2002/0045944 A1 | 4/2002 | Muhanna et al. | |

| | | |
|---|---|---|
| 2002/0077702 A1 | 6/2002 | Castro |
| 2002/0107573 A1 | 8/2002 | Steinberg |
| 2002/0111681 A1 | 8/2002 | Ralph et al. |
| 2002/0111684 A1 | 8/2002 | Ralph et al. |
| 2002/0111685 A1 | 8/2002 | Ralph et al. |
| 2002/0111686 A1 | 8/2002 | Ralph et al. |
| 2002/0111687 A1 | 8/2002 | Ralph et al. |
| 2002/0128714 A1 | 9/2002 | Manasas et al. |
| 2002/0128715 A1 | 9/2002 | Bryan et al. |
| 2002/0143399 A1 | 10/2002 | Sutcliffe et al. |
| 2002/0156528 A1 | 10/2002 | Gau et al. |
| 2002/0198598 A1 | 12/2002 | Pepper et al. |
| 2003/0004576 A1 | 1/2003 | Thalgott et al. |
| 2003/0009223 A1 | 1/2003 | Fehling et al. |
| 2003/0009224 A1 | 1/2003 | Kuras |
| 2003/0028251 A1 | 2/2003 | Mathews |
| 2003/0055427 A1 | 3/2003 | Graf |
| 2003/0069639 A1 | 4/2003 | Sander et al. |
| 2004/0002761 A1 | 1/2004 | Rogers et al. |
| 2004/0010316 A1 | 1/2004 | William et al. |
| 2004/0024462 A1 | 2/2004 | Ferree et al. |
| 2004/0102846 A1 | 5/2004 | Keller et al. |
| 2004/0133278 A1 | 7/2004 | Marino et al. |
| 2004/0133280 A1 | 7/2004 | Trieu |
| 2004/0143332 A1 | 7/2004 | Krueger et al. |
| 2004/0172021 A1 | 9/2004 | Khalili |
| 2004/0225366 A1 | 11/2004 | Eisermann et al. |
| 2004/0230309 A1 | 11/2004 | DiMauro et al. |
| 2004/0267369 A1 | 12/2004 | Lyons et al. |
| 2005/0033437 A1 | 2/2005 | Bao et al. |
| 2005/0043800 A1 | 2/2005 | Paul et al. |
| 2005/0119752 A1 | 6/2005 | Williams et al. |
| 2005/0159818 A1 | 7/2005 | Blain |
| 2005/0177239 A1 | 8/2005 | Steinberg |
| 2005/0192671 A1 | 9/2005 | Bao et al. |
| 2005/0197701 A1 | 9/2005 | Steinberg |
| 2006/0074489 A1 | 4/2006 | Bryan |
| 2006/0190082 A1 | 8/2006 | Keller et al. |
| 2007/0250169 A1 | 10/2007 | Lang |

FOREIGN PATENT DOCUMENTS

| | | |
|---|---|---|
| DE | 30 23 353 | 4/1981 |
| DE | 37 41 493 | 6/1989 |
| DE | 90 00 094.3 | 3/1991 |
| DE | 41 09 941 | 10/1992 |
| DE | 42 13 771 | 9/1993 |
| DE | 101 30 825 | 3/2002 |
| EP | 0 699 426 | 3/1996 |
| EP | 0 820 731 | 1/1998 |
| EP | 0 955 021 | 11/1999 |
| EP | 1 103 237 | 5/2001 |
| EP | 1 157 675 | 11/2001 |
| EP | 1 212 992 | 6/2002 |
| EP | 1 374 808 | 1/2004 |
| FR | 2 632 516 | 12/1989 |
| FR | 2 718 635 | 10/1995 |
| FR | 2 723 841 | 3/1996 |
| FR | 2 775 587 | 9/1999 |
| FR | 2 784 291 | 4/2000 |
| JP | 04099570 | 3/1992 |
| WO | WO 90/11740 | 10/1990 |
| WO | WO 94/04100 | 3/1994 |
| WO | WO 94/26213 | 11/1994 |
| WO | WO 99/11203 | 3/1999 |
| WO | WO 00/13620 | 3/2000 |
| WO | WO 01/64142 | 9/2001 |

* cited by examiner

CONTROLLED ARTIFICIAL INTERVERTEBRAL DISC IMPLANT

CROSS REFERENCE TO RELATED APPLICATION

The present application is a continuation of International Patent Application PCT/US03/25536 filed Aug. 15, 2003, which claims priority from U.S. Application No. 60/403,356 filed on Aug. 15, 2002 and U.S. Application No. 60/403,402 filed on Aug. 15, 2002, the entire contents of which are expressly incorporated herein by reference thereto.

FIELD OF THE INVENTION

The invention is related to devices and methods for the treatment of trauma and diseases of the spine. More particularly, the invention relates to intervertebral disc replacement.

BACKGROUND OF THE INVENTION

A variety of conditions such as spondylolysis, disc herniation, compression of spinal cord nerve roots, degenerative disc disease, and trauma are known to cause severe discomfort, requiring medical attention. Among the procedures currently used to alleviate such conditions are spinal fusion, such as intervertebral and posterolateral fusion or arthrodesis. In these procedures, two adjacent vertebral bodies are fused together. The affected intervertebral disc is first excised, and an implant is inserted which accommodates bone growth between the two vertebral bodies to effectively bridge the gap left by the disc removal. A number of different implant materials and implant designs have been used for fusion with varying success. Although intervertebral and posterolateral fusion are widely used, drawbacks to their use include a reduced physiologic range of motion and other fusion related complications such as degeneration of adjacent discs and destabilization of the functional spinal unit. As a result, alternative treatments with fewer complications, but similar efficacy to fusion, are desirable. One such alternative to spinal fusion is arthroplasty and the use of a prosthetic or artificial disc.

In general, arthroplasty is used in the replacement of diseased joints. Arthroplasty involves a set of procedures directed to maintaining motion of the joint, thereby preserving its integrity and keeping the adjacent motion segments from deteriorating, as they tend to do after fusion. Depending on the location and the condition of the affected joint, specific arthroplasty procedures may be used. For example, interpositional reconstruction surgery, which reshapes the joint and adds a prosthetic disk between the two bones forming the joint is commonly used on elbow, shoulder, ankle, and finger joints. Total joint replacement, or total joint arthroplasty, replaces the entire diseased joint with an artificial prosthesis and, in recent years, has become the operation of choice for most knee and hip problems.

Hip and knee replacements are particularly widespread with nearly 300,000 hip replacements and about as many knee replacements performed in the United States in 2001. With respect to the knee and hip joint replacement surgeries, there are several implants or prosthetics available. For the hip prosthetic, in an exemplary design, there are two components, one is a metal ball attached to a metal stem which is fitted into the femur, and the second is a matching plastic socket which is implanted into the pelvis. The metal pieces are generally formed from stainless steel, alloys of cobalt and chrome, titanium, and alloys of titanium; the plastic pieces are generally formed from high-density polyethylene. For the knee prosthetics, in an exemplary embodiment, metal and plastic components are again used to replace the damaged bone ends and cartilage. The metal pieces are generally formed from stainless steel, alloys of cobalt and chrome, titanium, and alloys of titanium; the plastic pieces are generally formed from high-density polyethylene.

Although the evolution of spinal arthroplasty and the use of prosthetics in the spine has been similar to that of other joints in the body, evolving from fusing the joint to replacing the functional joint, the advent of spinal athroplasty, however, has been slower than arthroplasty in other major joints in the body. A few of the possible reasons why spinal arthroplasty has been delayed are that spinal problems related to disc degeneration are difficult to diagnose, spinal procedures are typically crisis-driven and thus conservative solutions such as fusion are acceptable, and spinal anatomy is complex.

Over the past 40 years spinal arthroplasty technologies have been under development and in the last 10 years spinal arthroplasty has won the attention of leading surgeons and implant manufacturers. The evolution of spinal arthroplasty essentially began in the 1950's and one of several emerging concepts was the spherical concept of the disc prostheses. The spherical concept is simply the placement of a ball, essentially circumferential, in the cavity of the nucleus pulposus after a discectomy procedure has been performed. The annulus is kept in place and the ball serves as a nucleus replacement device. Various materials have been experimented with for the spherical concept. For example, in the early 1960's, implants using silicone ball bearings were implanted into the cervical regions of patients, but the outcomes were uncertain. In the mid 1960's, stainless-steel (ball bearing) prostheses were implanted into patients. The results of the procedure were initially promising but over time the disc spaces lost height due to subsidence of the steel balls into the vertebral bodies. Presently, the concept of a spherical prosthesis continues to be examined using different materials, the latest of which is a modified carbon fiber.

Another emerging concept is the mechanical concept design. The mechanical concept design is essentially a total disc replacement product which is intended to restore the range of motion of the vertebral motion segment unit. These devices are often comprised of metallic endplates fixed to the adjacent vertebral bodies via a stabilization mechanism and a core formed from polyethylene or other polymeric materials. Alternatively, instead of a core, bearing surfaces can be used, the bearing surface materials being ceramic-on-ceramic, metal-on metal, or metal-on-polyethylene. The mechanical design concept is based on the same principles as joint reconstruction products, such as knee and hip replacements, and a variety of mechanical design prostheses concepts have been proposed and continue to be proposed.

Another concept is the physiological concept. The physiological concept uses a hydrogel, elastomer, or polyurethane-based core which is intended to restore the disc function by absorbing and emitting fluid between the patient's vertebral endplates, while also maintaining the natural shock absorbing or cushioning function of the disc. The physiological concept devices are generally considered only a partial solution as they are designed to replace only the nucleus or a portion of the disc.

All of the approaches to disc replacement are aimed at some or all of the following: alleviating discogenic pain, restoring range of motion, maintaining the natural shock absorbing function of the disc, restoring normal form or disc height, and restoring physiological kinematics. Generally, four exemplary types of artificial intervertebral discs have been developed for replacing a portion or all of an excised disc: elastomer/fluid filled discs, ball and socket type discs, mechanical spring discs and hybrid discs.

Elastomer/fluid filled discs typically include an elastomer cushion or a fluid filled chamber positioned between lower and upper rigid endplates. The cushions and chambers of these implants advantageously function, in mechanical behavior, similar to the removed intervertebral disc tissue.

Ball and socket type discs typically incorporate two plate members having cooperating inner ball and socket portions which permit articulating motion of the members during movement of the spine.

Mechanical spring discs typically incorporate one or more coiled springs disposed between metal endplates. The coiled springs define a cumulative spring constant that is designed to be sufficient to maintain the spaced arrangement of the adjacent vertebrae while allowing normal movement of the vertebrae during flexion and extension of the spine in any direction.

The fourth type of artificial intervertebral disc, the hybrid disc incorporates two or more of the aforementioned design principles. For example, one known hybrid disc arrangement includes a ball and socket joint surrounded by an elastomer ring.

While each of the foregoing prostheses addresses some of the problems relating to intervertebral disc replacement, each of the implants presents significant drawbacks. Thus, there is a need for an intervertebral implant that accommodates the anatomy and geometry of the intervertebral space sought to be filled as well as the anatomy and geometry of the ends of adjacent vertebral bodies, while providing reliability and simplicity in design. More particularly, there is a need for a spinal disc implant which provides stability for supporting the high loads applied to the vertebrae, permits sufficient mobility to allow the patient an approximate normal range of motion, provides for axial compression between adjacent vertebrae, and has shock absorption abilities.

SUMMARY OF THE INVENTION

The invention relates to an intervertebral disc that is preferably designed to restore disc height and lordosis, allow for a natural range of motion, absorb shock and provide resistance to motion and axial compression. Furthermore, the intervertebral disc may be used in the cervical, the thoracic, or the lumbar regions of the spine.

The intervertebral disc includes a body having a footprint that is preferably conforming in size and shape with at least a portion of the ends of adjacent vertebrae. The shapes of the intervertebral disc include, but are not limited to, circular, oval, ellipsoid, kidney-bean, annular, C-shaped, D-shaped, etc.

In one embodiment, the intervertebral disc includes an upper endplate, a lower endplate, and an intermediate elastic membrane disposed between the upper and lower endplates. Alternatively, the elastic membrane may surround and encapsulate the endplates. The elastic membrane in combination with the upper and lower endplates defines an interior volume. The interior volume of the disc includes at least one spring element, the spring element being attached to the upper and lower endplates. Preferably, the spring element is attached to the lower endplate within a pocket or groove formed on the inner surface of the lower endplate, while the upper end of the spring element is attached to a hemi-spherical member. The hemi-spherical member is designed to mate with and articulate in a socket formed on the inner surface of the upper endplate.

Alternatively, the disc may be provided with a plurality of spring elements with each spring element extending from the upper endplate to the lower endplate, and each spring element may have a hemi-spherical members on both ends to mate with corresponding sockets formed on the inner surface of the upper and lower endplates. The disc may also be configured such that the disc generally contains a first spring element surrounded by a plurality of second spring elements uniformly spaced around the first spring element. The first spring element preferably having a stiffness and/or spring constant which is greater than the stiffness of the periphery spring elements.

Furthermore, the disc may include a plurality of spring element, whereby only a portion of the spring elements may be attached to a hemi-spherical member, with the remaining spring elements being attached to the upper and lower endplates, preferably in pockets. In one exemplary embodiment, the first spring element with be attached to a hemi-spherical member while the surrounding peripheral second spring elements will be attached directly to the upper and lower endplates.

The disc may also include an elastomeric strut or ring in place of one or all of the spring elements. Furthermore, the disc may incorporate casing members.

The disc may also include a fluid disposed within the interior volume and a valve for permitting insertion of and removal of the fluid.

The upper and lower endplates are preferably formed of metal, such as titanium, stainless steel, titanium alloys, cobalt-chromium alloys, or amorphous alloys. Alternatively, however, the upper and lower endplates may be formed of ceramics, composites, polymers, such as poly-ether-ether-ketone (i.e., PEEK) or an ultra high molecular weight polyethylene (i.e., UHMWPE), bone, including cortical, cancellous, allograft, autograft, xenograft, demineralized or partially demineralized bone, or any other materials able to serve as load bearing supports. The materials chosen for the endplates, in combination with the desired fluid, are preferably selected to reduce the amount of wear, and thus increase the life of the joint.

The outer surface of the upper and lower endplates may be substantially flat, wedge-shaped, etc. The outer surfaces of the upper and lower endplates may also be dome shaped with their radii defined in the sagittal and coronal planes to generally match those of the ends of the adjacent vertebra. The dome shape allows the upper and lower endplates to better conform with the ends of the adjacent vertebrae for a better fit in situ.

The intervertebral disc also preferably includes migration-resistant structures provided on the outer surface of at least one or both of the endplates to impede movement, dislodging, or expulsion of the endplates within and from the ends of the adjacent vertebrae. The migration-resistant structures include, but are not limited to, flaps, spikes, teeth, fins, deployable spikes, deployable teeth, flexible spikes, flexible teeth, alternatively shaped teeth, insertable or expandable fins, screws, hooks, serrations, ribs, and textured surfaces.

Furthermore, the upper and lower endplates also preferably coated with a bone growth inducing or conducting substance to promote bony ingrowth to permanently secure the disc to the adjacent vertebrae. Alternatively, the upper and lower endplates may have a roughened surface; a porous surface; laser treated endplate layers; integrate an osteoconductive/osteoinductive scaffold; or may be provided with or made from an integral osteoconductive and/or osteoinductive material to promote bony ingrowth. The endplates may further include a membrane and/or a barrier to limit the amount and/or depth of bony ingrowth.

The upper and lower endplates may also have implant instrumentation attachment, guiding, and retainment structures. For example, the endplates may have holes, slots, threads, or a dovetail for implanting the implant and/or distracting the adjacent vertebrae. For example, the disc may include a slot formed in the upper and/or lower endplates, the slot being configured to receive an implant insertion instrument, a distractor or both.

The upper and lower endplates may also preferably include articulating surfaces, thus providing the intervertebral disc with greater mobility. The articulating surfaces preferably including a surface polish or similar wear reducing finish such as diamond finish, TiNi finish, etc. in order to minimize wear, decrease particle generation, and increase disc life.

In some embodiments, the interior of the disc may include a leaf spring attached on one end to the upper and/or lower endplate but unattached on the other end. Disposed between the ends, the leaf spring preferably includes an enlarged convex intermediate section which mates, articulates, and slides with the inner surface of one of the endplates. Preferably, the unattached end of the leaf spring is attached to a roller by means of an axle, the axle allowing the roller to freely rotate thus permitting the leaf spring to move freely during the flexing of the spring.

In some embodiments, the interior volume of the disc includes an articulating member which is attached to the upper or lower endplate. The articulating member preferably being attached to one of the endplate by an intermediate shock absorbing layer. The shock absorbing layer preferably being an elastomer, polymer fibers, polyurethane, silicone, or other suitable elastic material having shock absorbing properties.

In other embodiments, the disc generally includes an upper endplate, a lower endplate, and a flexible core disposed between the upper and lower endplates, preferably within pockets containing mating surfaces. The flexible core preferably is either a slotted core, a ring spring, a winged leaf spring, or a leaf spring. The flexible member may be dimensioned and configured to provide flexion/extension, lateral bending, axial rotation, and/or translation, depending on the loading conditions imparted on the intervertebral disc.

The intervertebral disc may be implanted in a modular fashion, if possible, or may be implanted preassembled. An anterior, anteriolateral, or lateral surgical approach may be used for the intervertebral disc. Furthermore, depending on the intervertebral disc to be implanted, a minimally invasive surgical method and/or a simultaneous distraction and implantation surgical method may be used. Also depending on the intervertebral disc to be implanted, the Anterior Longitudinal Ligament may be attached directly to the disc or to the adjacent vertebral bodies. The Anterior Longitudinal Ligament may be formed from partially demineralized or demineralized autograft, allograft, or xenograft. Alternatively, the Anterior Longitudinal Ligament may be formed from biocompatible materials such as elastomers, or braided polymers. To assist with the implantation of the intervertebral disc, the intervertebral disc may include alignment markers.

BRIEF DESCRIPTION OF THE DRAWINGS

To facilitate an understanding of and for the purpose of illustrating the present invention, exemplary and preferred features and embodiments are disclosed in the accompanying drawings, it being understood, however, that the invention is not limited to the precise arrangements and instrumentalities shown, and wherein similar reference characters denote similar elements throughout the several views, and wherein:

FIG. 9b is an exploded view of the seventh embodiment shown is FIG. 9a;

FIG. 9c is an exploded view of the seventh embodiment shown is FIG. 9a; and

DETAILED DESCRIPTION OF THE PREFERRED EMBODIMENTS

Figure 1:
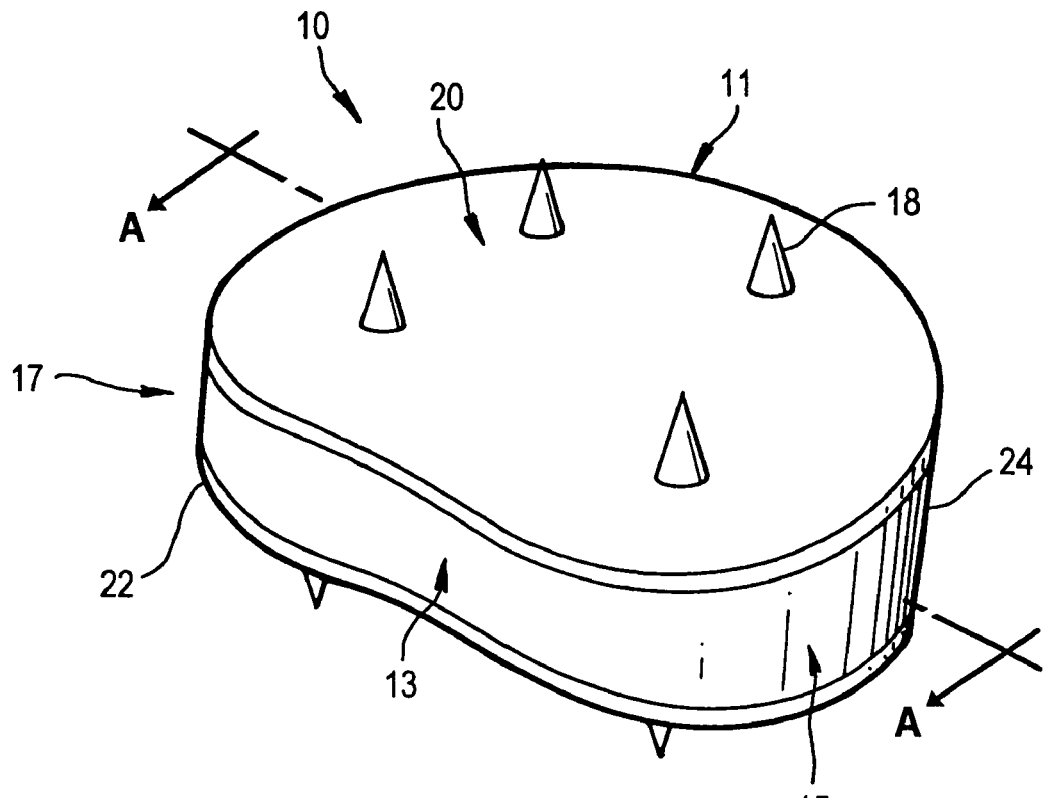
FIG. 1 is a perspective view of a first embodiment of an artificial intervertebral disc according to the present invention.

Any of a wide variety of different implant structures can be prepared according to the teachings shown by the illustrative examples of the intervertebral discs disclosed herein. The intervertebral discs of the present invention are preferably designed to restore the natural spinal curvature (or sagittal balance), disc height, to allow for a natural range of motion, absorb shock and to provide resistance to motion and axial compression.

The intervertebral discs preferably are sized and adapted for use in the cervical, thoracic, and lumbar regions of the spine. Also, the intervertebral discs can be tailored for each individual patient allowing for disc characteristics appropriate for the individual patient. For example, and artificial disc may be provided having a pair of endplates and a core, and the core of the disc can include different assemblies, different components, and/or various types of materials to create the desired dynamic characteristics for each individual patient.

Furthermore, the intervertebral discs may allow flexion, extension, lateral bending, rotation, and translation. Flexion is movement that brings two parts of a joint or body into a bent position; in the spine, this is a movement in which the spine starts straight and moves into forward bending. Extension is a movement that draws two parts away from each other; in the spine, this is a movement in which the spine starts straight and moves into backward bending. Lateral bending is a bending movement toward a lateral side; in the spine, this movement generally involves bending (lateral) and coupled rotation. Rotation is a movement that results in a portion of the spine twisting, rotating or turning with respect to the axis of the spinal column. Translation is a limited movement that is generally transverse to the axis of the spinal column.

Additionally, similar to a natural intervertebral disc, the artificial intervertebral discs preferably allow for a moving instantaneous axis of rotation. At every instant for a body in plane motion there is a line in the body or a hypothetical extension of this line that does not move. The instantaneous axis of rotation is this line. A moving instantaneous axis of rotation refers to the ability of the instantaneous axis of rotation to move (i.e., translate) as a result of different loading conditions; in other words, the location of the instantaneous axis of rotation moves with respect to the disc. The preferred mean location of the moving instantaneous axis of rotation for the lumbar region of the spine is preferably in the posterior half of the disc space or proximal to an adjacent (superior or inferior) endplate, preferably proximal to the inferior/caudal endplate, the preferred mean location of the moving instantaneous axis of rotation for the thoracic region of the spine is preferably in the inferior portion of the disc space and proximal to the caudal vertebral body extending posteriorly into the spinal canal, and the preferred mean location of the moving instantaneous axis of rotation for the cervical region of the spine is preferably in the posterior half of the caudal vertebral body.

Also similar to a natural intervertebral disc, the response characteristics of the artificial intervertebral disc are preferably non-linear. For example, in response to continued axial compression, the artificial intervertebral disc preferably undergoes a large initial amount of compression followed by non-linearly decreasing amounts of compression.

Referring to the accompanying drawings, preferred embodiments and features of the artificial intervertebral disc will be described in detail. It is to be noted however that these descriptions of specific embodiments and features are merely illustrative. It is contemplated that one or more features or elements of the various embodiments may be combined or used singularly, and that modifications of the various embodiments, as well as other embodiments are contemplated and will be apparent to those persons skilled in the art.

Referring initially to FIG. 1, a perspective view of an exemplary first embodiment of an artificial disc 10 is shown. Disc 10, preferably, has a generally kidney-bean shaped footprint which includes an anterior side 11, a posterior side 13, and first and second lateral sides 15, 17, respectively. Anterior side 11 and lateral sides 15, 17 are all substantially convex in shape while posterior side 13 is substantially concave in shape. However, the disc 10 may take on other shapes that generally conform geometrically and anatomically with the adjacent vertebral bodies including, but not limited to circular, oval, ellipsoid, annular, D-shaped, C-shaped, etc.

As shown, disc 10 includes an upper endplate 20, a lower endplate 22, and an intermediate elastic membrane 24, the elastic membrane 24 generally extending from the upper endplate 20 to the lower endplate 24, preferably, proximate the outer periphery of the disc 10. Alternatively, the elastic membrane 24 may surround and encapsulate the upper and lower endplates 20, 22. The elastic membrane 24 in combination with the upper and lower endplates 20, 22 define an interior volume 26.

The elastic membrane 24 preferably is formed from an elastomer such as polyurethane, silicone, a braided polymer, or any other appropriate elastic material. The elastic membrane 24 may be permeable or semi-permeable to allow fluid to flow into and out of the interior of the disc (as described in more detail below). Alternatively, the membrane may be non-permeable. Preferably, the elastic membrane 24 may resist translational motion between the upper and lower endplates 12, 14, and may also prevent soft tissue ingrowth between the endplates 12, 14 as well as contain any wear particles generated within the interior volume. The elastic membrane 24 may be attached to the upper and lower endplates 12, 14 by any fixation method known in the art including, but not limited to, bonding agents, ultrasonic welding, screws, nails, mechanical wedging, and pins.

Alternatively, the elastic membrane 24 may be in the form of a bellow, the bellow assuming an "accordion" or other flexible shape, enabling it to expand and contract under the various loading conditions. The bellow may be rigidly attached to the upper and lower endplates 12, 14 by any method known in the art including, but not limited to a circular groove formed in each endplate 12, 14, bonding agents, ultrasonic welding, screws, nails, mechanical wedging, and pins. Preferably, the bellow is made from a metal, although other material such as elastomers or polymers may be used. In an alternative embodiment, membrane 16 may be made of any appropriate non-elastic material known in the art.

Figure 2:
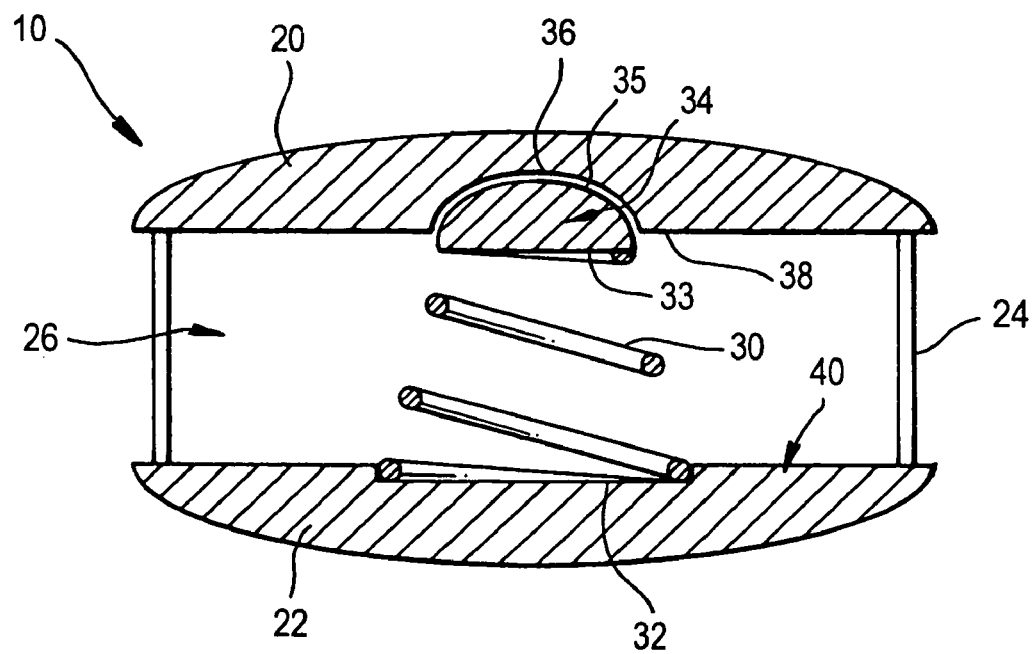
FIG. 2 is a cross-sectional view of the artificial intervertebral disc of FIG. 1 taken along line A-A.

With reference to FIG. 2, the interior 26 of disc 10 is shown. Preferably, the interior 26 of the disc 10 includes at least one spring element 30, and the spring element 30 may have a longitudinal axis. The spring may be oriented such that its longitudinal axis is oriented substantially perpendicular to the plane formed by each of the upper and lower endplates 20, 22. Alternatively, the spring may be oriented such that its axis forms an acute angle with at least one of the upper and lower endplates. The spring element may have a first end which contacts the lower endplate 22 within a pocket or groove 32 formed on the inner surface 40 of the lower endplate 22. Such a pocket or groove may prevent lateral displacement of the spring with respect to the endplate. An upper end of the spring element 30 may engage an articulation member 34 having a spring-engaging surface 33 and an opposite substantially spherical surface 35. The spring element 30 may be fixed to the pocket 32 and/or the articulation member 34 using any appropriate fixation method known in the art including, but not limited to bonding agents, ultrasonic welding, screws, nails, press-fit, and pins. Alternatively, the spring element 30 and the articulation member 34 may be integrally formed.

The spherical surface 35 of articulation member 34 may be configured to articulate within a correspondingly shaped socket 36 formed on the inner surface 38 of the upper endplate 20. The interface between the articulation member 34 and the socket 36 may approximate a ball and socket type connection, with the spherical articulation member 34 able to articulate within the socket 36. The type and amount of articulation desired may dictate the curvature and arc of the spherical surface 35 provided on the articulation member 34 and socket 36. For example, if the spherical surface 35 has the same radius as the socket 36, then the disc 10 may provide greater support but more constrained movement. Alternatively, if the socket 36 has a larger radius than the spherical surface 35, the disc 10 may provide increased articulation and/or translation.

In an alternative embodiment, the socket 36 may incorporate a flattened portion which may permit the articulation member 34 to translate within the socket, thereby providing translational movement of the upper endplate 20 relative to the lower endplate 22. By providing for such translation, the disc 10 may provide a moving instantaneous axis of rotation. It is possible for the articulation member 34 and socket 36 to have contours other than spherical in order to achieve the desired articulation motion. Such other contours may comprise elliptical or egg-shaped, and multiply-spherical shaped in which the articulation member and the socket each may comprise at least two separate or cojoined spherical segments. Moreover, while the articulation member 34 and socket 36 are illustrated as having contours that generally permit mating of their respective surfaces, the corresponding surfaces may take on any appropriate shape to achieve the desired articulating mobility between the upper and lower endplates 20, 22.

While the disc 10 has been described as having the articulating member 34 associated with the lower endplate 22 and the socket 36 associated with the upper endplate 20, the elements may be reversed so that the socket 36 and articulating element 35 are instead associated with the lower and upper endplates, respectively. Furthermore, the socket member may be provided integral with its respective end plate, such as providing a one-piece end plate with a hollow spherical inner surface. Also, the socket member and articulating element may comprise any appropriate material known in the art, such as titanium, stainless steel, polymers such as ultra high molecular weight polyethylene, etc. Furthermore, the articulating surfaces may include a surface polish or similar wear reducing finish such as diamond finish, TiNi finish, etc. in order to minimize wear, decrease particle generation, and increase disc life.

The spring element 30 may encompass any appropriate resilient member known in the art including, but not limited to, spiral springs, coil springs, plate or leaf springs, etc. Moreover, the spring element 30 may be formed from any appropriate material known in the art including, for example, polymers, composites, or metals such as cobalt-chromium alloys, titanium alloys, stainless steel, shape memory alloys, and amorphous alloys. Likewise, the spring element 30 may comprise two or more individual spring elements provided either in series, in parallel, or in a combination of series and parallel elements.

The selection of a particular spring element may depend on the needs of the particular patient, however, the spring or springs selected should mimic the properties of the patient's normal intervertebral disc, or should be appropriate as required for the particular procedure. Thus, springs having the appropriate stiffness in axial compression and in transverse bending should be selected to provide the following ranges: flexion/extension—from about 0 Newton-meters per degree (Nm/deg) to about 8 Nm/deg); lateral bending—from about—Nm/deg to about 5 Nm/deg; and compression—from about 100 to about 5000 N/mm. Furthermore, the outer diameter of the springs selected may range from about 5 millimeters (mm) to about 30 mm; and the heights of the springs may range from about 7.5 mm to about 12 mm. It is noted that the preceding are provided as representative dimensions only, and the springs used may have any size, shape, strength and flexibility appropriate for the particular patient.

The use of a spring element in combination with an articulating surface may provide a combination of articulation, translation and compression/shock absorption between the upper and lower endplates 20, 22, and thus allowing for a moving instantaneous axis of rotation. Articulation may be provided through the interaction of the articulating member 35 and the socket 36, and/or by bending of the at least one spring element 30. Compression and shock absorption may be provided by the spring element 30, and translation may be provided by bending of the spring element or through the choice of a socket having a flattened portion such that the articulating member 36 may translate within the socket.

Figure 2A:
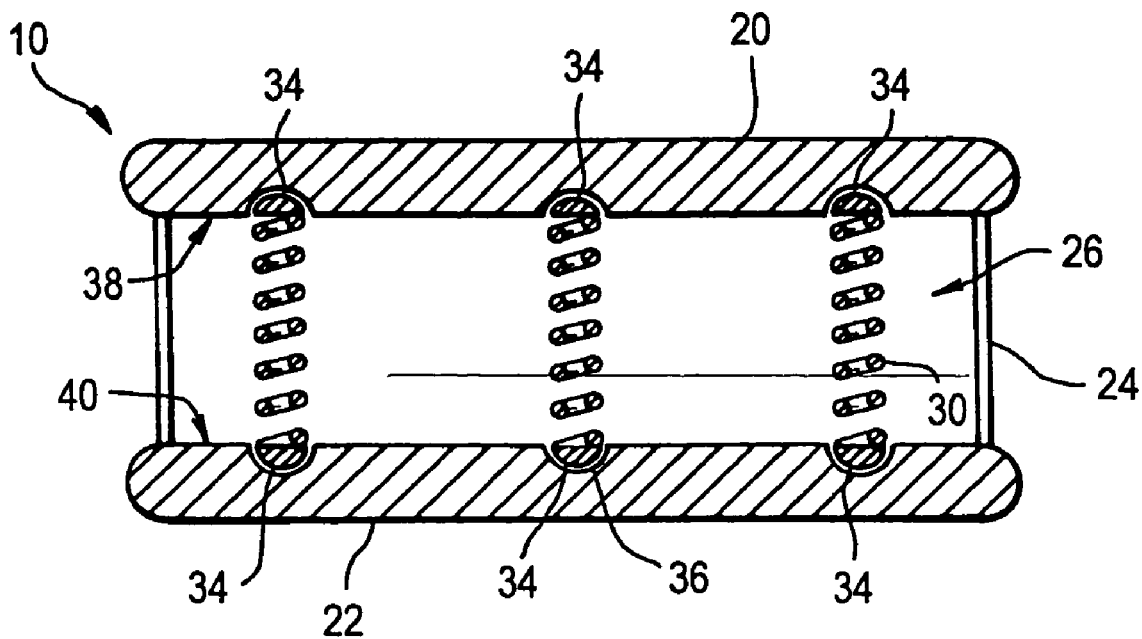
FIG. 2a is an alternate cross-sectional view of the artificial intervertebral disc of FIG. 1 taken along line A-A.

Referring to FIG. 2a, a disc 10 comprising a plurality of internal spring elements 30 is illustrated, each spring element 30 may extend from the upper endplate 20 to the lower endplate 22 such that the longitudinal axis of each spring element is oriented substantially perpendicular to the plane formed by each of the end plates 20, 22. Alternatively, one or more of springs 30 may be oriented so that their longitudinal axis forms an acute angle relative to the plane of one or both of the end plates.

The plurality of spring elements 30 may be arranged in a configuration appropriate to provide uniform shock absorption, load bearing, and tension/compression resistance, or the spring elements 30 may be strategically placed to allow for increased resistance to shock and/or compression on one side (i.e. anterior, posterior) of the disc as compared to the other. Preferably, however, the disc 10 includes at least one central spring element 30 and at least one peripheral spring element 30 spaced away from the central spring element 30. In the illustrated embodiment, a single central spring element is surrounded by a plurality of peripheral spring elements. The central and peripheral spring element 30 may have substantially the same stiffness, or their stiffnesses may be different. Preferably, the central spring element 30 may have a stiffness greater than the stiffness of the peripheral spring elements 30. Such an arrangement may result in a disc having a central spring which provides primary shock absorption and resistance during the initial stages of an axial compression evolution, and having peripheral spring elements 30 which provide secondary shock absorption and resistance during the later phases of axial compression. This provides a desirable non-linear response to compressive loads which may closely mimic the response of the patient's natural disc.

As shown in FIG. 2a, each spring element 30 has first and second ends associated with respective upper and lower end plates 20, 22. The first and second ends of each spring may have an associated spherical articulation member 34 configured to mate with a corresponding spherical socket 36 formed on the inner surface of the upper and lower endplates 20, 22 as previously described. The combination of spring and articulation members permits the upper and lower endplates 20, 22 to move with respect to each other. For example, articulation members 34 may articulate within associated sockets 36 so that the upper and lower endplates 20, 22 can articulate with respect to each other without creating resistive torsion in spring elements 30 that would be present if the ends of the springs were rigidly connected to the endplates. Alternatively, each spring element 30 may only be attached to a spherical member 34 on one end, the other end being attached to the upper or lower endplate 20, 22 as previous described.

Figure 2B:
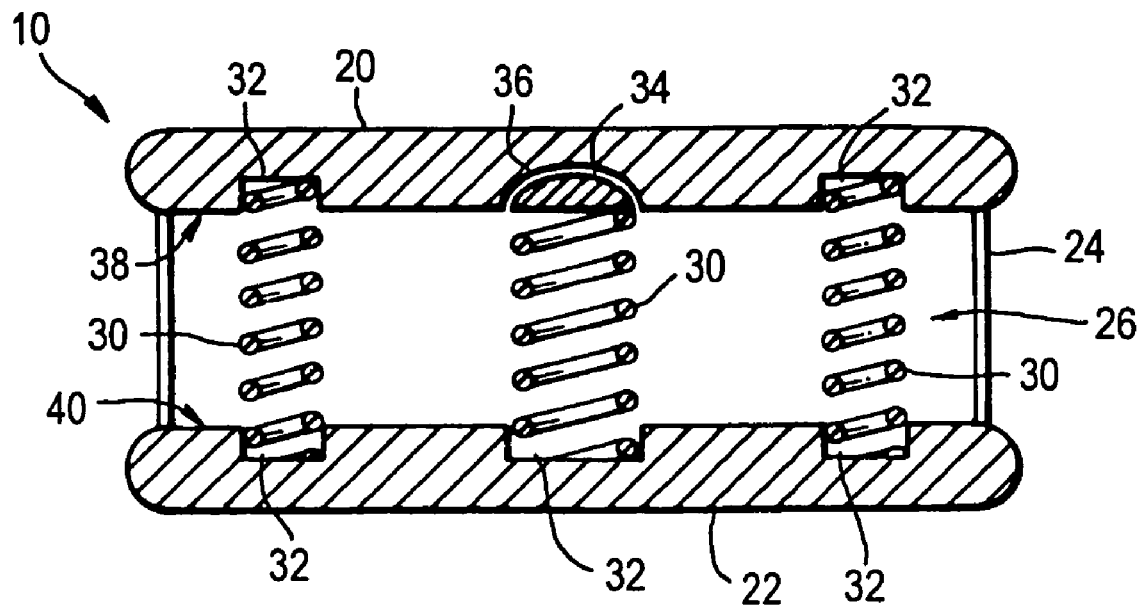
FIG. 2b is an alternate cross-sectional view of the artificial intervertebral disc of FIG. 1 taken along line A-A.

Referring to FIG. 2b, the disc 10 may include a plurality of spring elements 30 where only one end of the first spring element 30 comprises a spherical articulation member 34, and the opposite end of the first spring element 30 as well as both ends of the second spring elements 30 are disposed within corresponding pockets, or recesses, in the upper and lower endplates 20, 22 (the arrangement and connection of these recesses and the associated spring elements being the same as previously described in relation to the embodiment of FIG. 2). As shown in FIG. 2b, preferably the first spring element 30 is attached to a hemi-spherical member 34 for mating with a corresponding socket 36 located in the upper or lower endplate 20, 22. The plurality of second spring elements 30 surrounding the first spring element 30 being attached directly to the upper and lower endplates 20, 22 as previously described. In one embodiment, the first spring may be attached to one hemi-spherical member 34, and the plurality of second spring elements 30 may be may be attached to two hemi-spherical member 34. As with the previous embodiments, the number, stiffness, and arrangement of the springs, as well as the selection and placement of the articulating elements and sockets 36 may be made in any combination appropriate to provide a disc that mimics as closely as possible the properties of the normal intervertebral disc, or that provides the properties appropriate to the particular procedure.

Figure 2C:
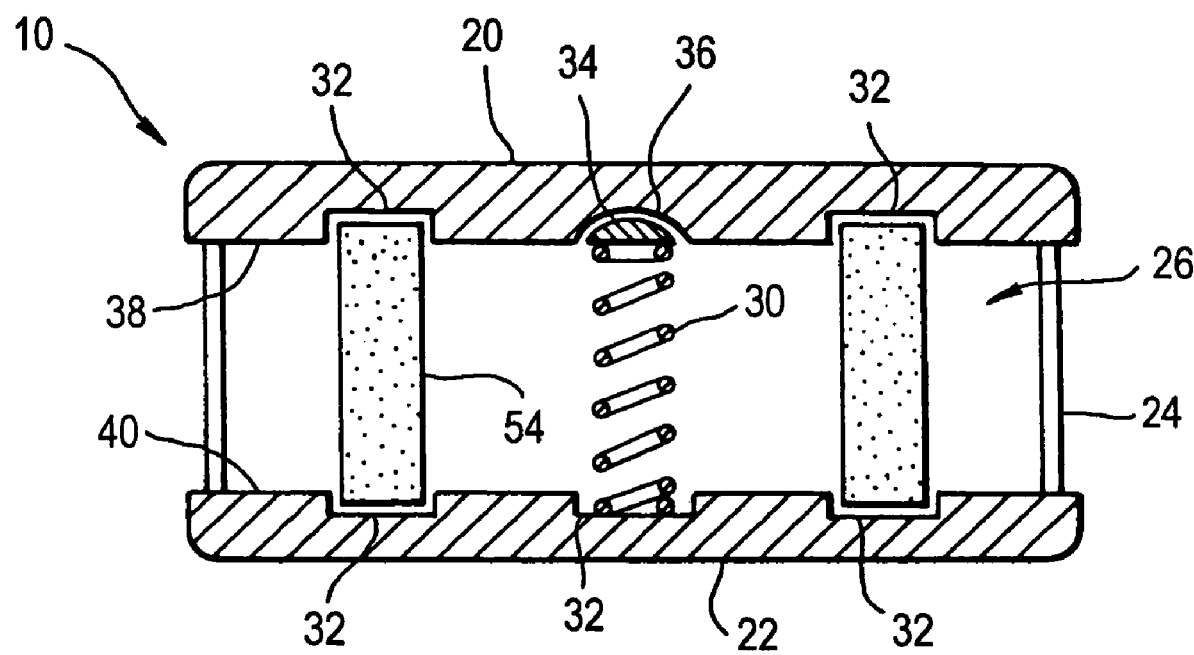
FIG. 2c is an alternate cross-sectional view of the artificial intervertebral disc of FIG. 1 taken along line A-A.

Referring to FIG. 2c, the disc 10 may include an elastomeric strut 54 located peripherally to a central spring element 30. The strut 54 may have a longitudinal axis and first and second ends, and each end may be associated with an upper or lower endplate 20, 22. The elastomeric strut 54 may be seated in a groove 32 formed in the associated inner surfaces 38, 40 of the upper and lower endplates 20, 22 to resist displacement. The elastomeric strut 54 may serve essentially the same function as peripheral spring elements 30 previously described, i.e. to provide the disc 10 with compression force resistance and shock absorption and to resist motion. The elastomeric strut 54 may be formed from any appropriate material known in the art including, but not limited to, polyurethane or silicone. Any number of individual struts 54 may be provided, and the struts individual struts may assume various shapes in order to provide the appropriate stiffness or resistance support for the end plates. Thus, the struts 54 may be cylindrical, square, rectangular, etc., and they may have any appropriate cross section, such as circular, triangular, elliptical, etc. The struts may also be provided with continuous or non-continuous cross-sections, and they may be made up of different layers of materials, such as having alternating elastomeric and metallic or polymer layers. The struts 54 may also be hollow, or they may be ring-shaped. The ring-shaped struts 54 may be configured to surround at least a portion of the first spring element 30. As with earlier embodiments, the ends of struts 54 may be connected to the end plates using any appropriate method in the art, including press-fit, bonding agents, etc. One or more struts may also be provided to move within their associated groove or grooves. The arrangement, number and configuration of the struts 54 is not critical, but instead may be any combination desired to provide a disc 10 that mimics the properties of the patient's normal intervertebral disc, or that provides the properties appropriate to the particular procedure.

The inner surfaces 38, 40 of endplates 20, 22 may be porous to allow the elastomeric strut 50 to be integrated into the corresponding surfaces of the upper and lower endplates 20, 22 during manufacture such as by molding the elastomer to the endplate. A membrane and/or barrier may also be included within endplates 20, 22 to limit the depth of impregnation and bony ingrowth respectively.

The disc 10 of this embodiment also may include a membrane 24 and a valve (not shown), the valve providing access to the interior 26 of disc 10 so that fluid may be injected into, or removed from, the interior 26 of the disc 10. The valve preferably is a one-way valve, as known to those skilled in the art, so that the fluid, once injected, can not escape from the interior 26 of the disc 10. Preferably, the valve is disposed through the elastic membrane 24, alternatively however, the valve may be disposed through the upper and/or lower endplates 20, 22. When the valve is disposed on the upper and/or lower endplates 20, 22, a passageway preferably is included to interconnect the valve with the interior 26 of the disc 10.

The fluid may be a gas, a liquid, a gel, or any combination thereof, that is sufficient to provide shock absorption during axial compression of the disc 10, while also permitting limited articulation or movement of the upper endplate 20 and lower endplate 22 with respect to one another. Preferably, the fluid is incompressible, for example, saline or mineral water. In use, the fluid may be injected into the interior 26 of the disc 10 before insertion of the disc 10 between adjacent vertebrae. Alternatively, the fluid may be injected in situ to facilitate insertion of disc 10 and subsequent distraction between adjacent vertebrae. The rigidity and distraction capability of the disc 10 may be a function of the amount of fluid injected into the interior 26 of the disc 10. Generally, the more fluid provided in the interior 26 of the disc 10, the more rigid the disc 10, and the greater the distraction capability. Furthermore, pliability and increased articulation may be realized by filling only a portion of the interior 26 of the disc 10. Finally, variably filling the interior 26 of the disc 10 with fluid permits the overall height H of the disc 10 to be varied as necessary depending on the needs of the individual patient.

Depending on the location of the spine where the disc 10 is implanted, the disc 10 preferably restore height in the range between about 4 millimeters to about 26 millimeters. In addition, the disc 10 preferably restore lordosis in the range between about 0° to about 20°. The disc 10 preferably also restore stiffness from about 1 Nm/deg to about 11 Nm/deg in axial rotation, about 0 Nm/deg to about 7 Nm/deg in flexion/extension, and about 0 Nm/deg to about 5 Nm/deg in lateral bending. In addition, the disc 10 preferably offers compression stiffness from about 100 N/mm to about 5000 N/mm and tension stiffness from about 50 N/mm to about 1000 N/mm. Furthermore, depending on the location of the spine where the disc 10 is implanted, the intervertebral disc 10 preferably allows for a range of motion of about 5° to about 45° in flexion/extension, of about 3° to about 33° in lateral bending, and about 1° to about 60° in axial rotation. The intervertebral disc 10 preferably also allows for axial compression in the range from about 0.2 mm to about 2 mm.

Preferably, the upper and lower endplates 20, 22 are formed of metal, such as titanium, stainless steel, titanium alloys, cobalt-chromium alloys, shape memory alloys, or amorphous alloys. Alternatively, however, the upper and lower endplates 20, 22 may be formed of polymers including rigid polymers, PEEK or UHMWPE, ceramics, composites, bone including cortical, cancellous, allograft, autograft, xenograft, demineralized or partially demineralized bone, or any other material appropriate to serve as load bearing supports. More preferably, the materials chosen for the endplates are chosen so as to minimize wear.

Furthermore, preferably, any articulating surfaces in the intervertebral discs of the present invention include a surface polish or similar wear reducing finish such as diamond finish, TiNi finish, etc. in order to minimize wear, decrease particle generation, and increase disc life.

The outer surface of the upper and lower endplates 20, 22 may be substantially flat, wedge-shaped, etc. The outer surfaces of the upper and lower endplates 20, 22 may also be dome shaped with their radii defined in the sagittal and coronal planes to generally match the shape of the ends of the adjacent vertebral, thereby providing a better fit in situ.

Figure 3A:
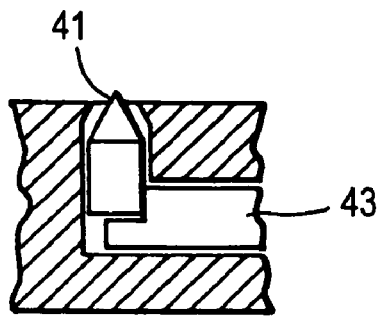
FIG. 3a is a side view of a deployable spike according to the present invention.
Figure 3B:
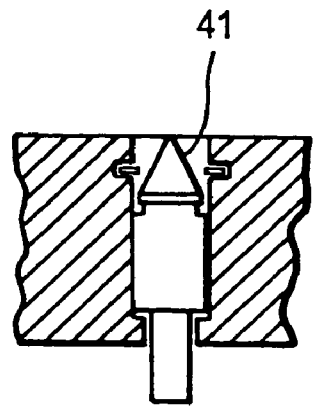
FIG. 3b is a side view of another deployable spike according to the present invention.
Figure 3C:
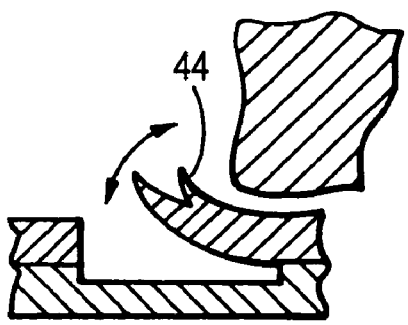
FIG. 3c is side view of a flexible spike according to the present invention.
Figure 3D:
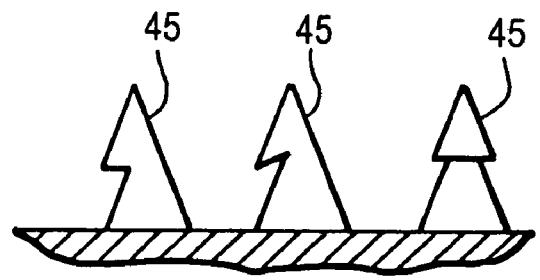
FIG. 3d is a side view of alternatively shaped teeth according to the present invention.
Figure 3E:
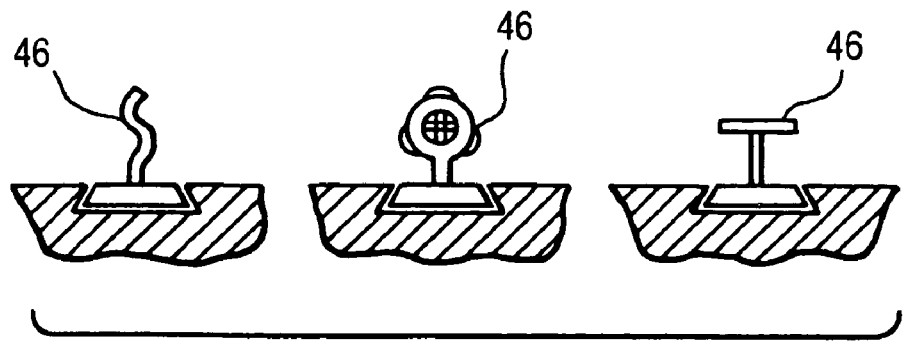
FIG. 3e is a side view of anchors according to the present invention.

In addition, as shown in FIG. 1, the disc 10 may include migration resistant features, such as, for example, spike-like structures 18 on the outer surfaces of the upper and lower endplates 20, 22. The migration resistant features may facilitate engagement of the disc 10 with the ends of the adjacent vertebra by providing a mechanical interlock as a result of penetration and/or deformation of the ends of the adjacent vertebrae. The initial mechanical stability afforded by spikes 18, for example, minimizes the risk of post-operative instability, movement, dislodging or expulsion of the disc 10. Other migration resistant features may include, without limitation, flaps, teeth, deployable teeth, deployable spikes, flexible spikes, flexible teeth, fins, insertable or expandable fins, anchors, screws, ridges, serrations, or other similar texturing on the upper and lower endplates 20, 22. As shown in FIG. 3a, deployable spikes 41 may be provided, and a cam mechanism 43 may be used to deploy the spikes. Alternatively, as shown in FIG. 3b, the deployable spikes may be configured to be deployed by an instrument (not shown). As shown in FIGS. 3c through 3e, respectively, examples of flexible spikes 44, shaped teeth 45, and anchors 46 are shown. Alternatively or in addition, bonding agents may also be used to secure the disc 10 to adjacent vertebra.

Furthermore, the upper and lower endplates 20, 22 may also be coated with a bone growth inducing substance, such as hydroxyapatite, to promote bony ingrowth to permanently secure the disc 10 to the adjacent vertebrae. Alternatively, the upper and lower endplates 20, 22 may have a roughened or porous surface to facilitate bony ingrowth. Alternatively, the upper and lower endplates 20, 22 may have laser treated endplate layers to create a porous structure, or may integrate an osteoconductive/osteoinductive scaffold. The endplates 20, 22 may also be made from an osteoconductive and/or osteoinductive material to promote bony ingrowth. The endplates 20, 22 may further include a membrane and/or barrier to limit the depth of bony ingrowth permitted.

The upper and lower endplates 20, 22 may also have implant instrumentation attachment, guiding, and retaining structures. For example, the endplates 20, 22 may have holes, slots, threads, or a dovetail for accepting a tool used to implant and/or distract the vertebrae. For example, the disc may include a slot formed in the upper and/or lower endplates 20, 22, the slot configured to receive an implant insertion instrument, a distractor or both.

As a result of the material and structural components used, the disc 10 can allow flexion/extension, lateral bending, axial rotation, and translation, depending on the loading imparted on the intervertebral disc. In addition, under various spinal loading conditions resulting from spinal movements, the spring element 30 can compress, tilt, articulate and/or bend varying amounts.

Figure 4:
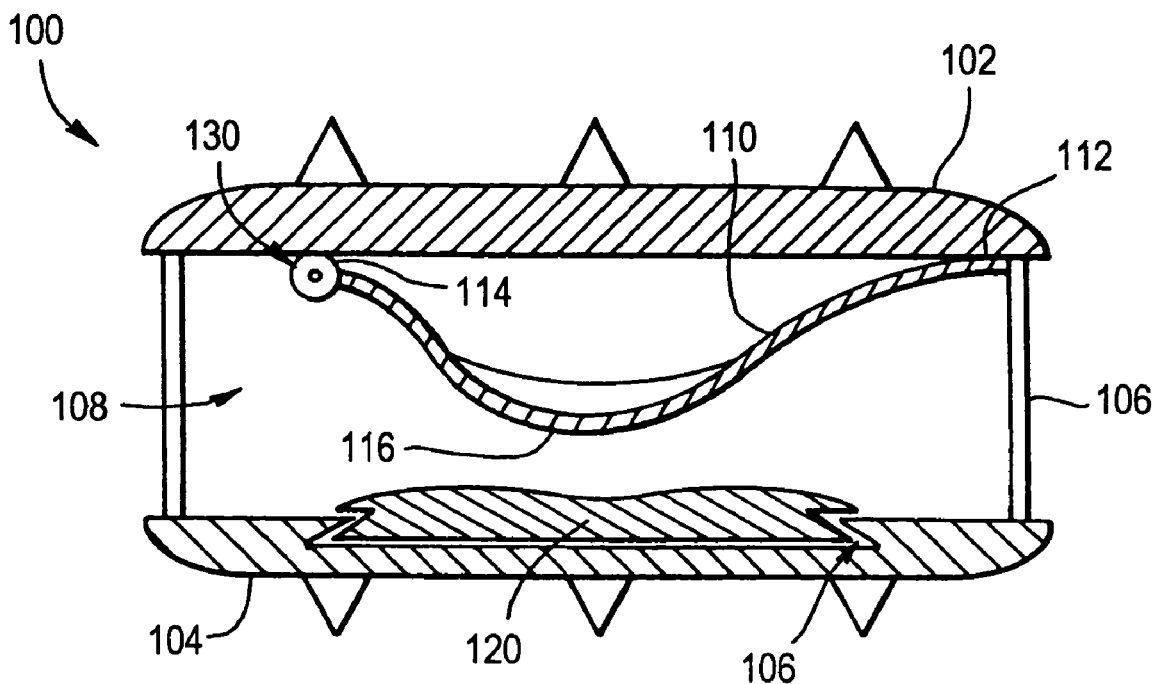
FIG. 4 is a cross-sectional view of a second embodiment of an artificial intervertebral disc according to the present invention.
Figure 4A:
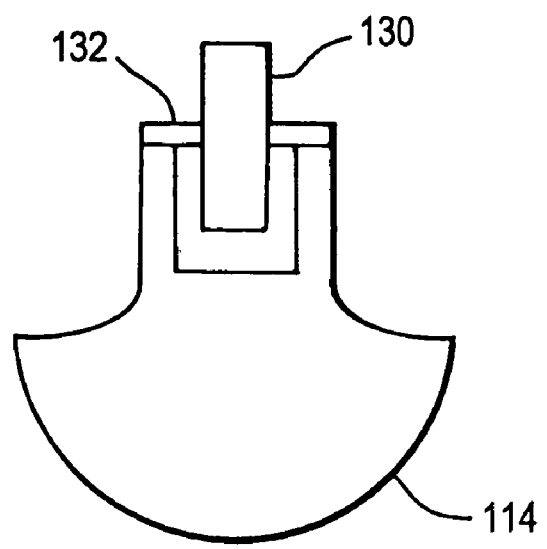
FIG. 4A is a side view of the leaf spring and roller of the artificial intervertebral disc of FIG. 4.

With reference to FIGS. 4 and 4a, a second exemplary embodiment of an intervertebral disc 100 is shown. Similar to the previous embodiments described, the external configuration of disc 100 may take on any shape that generally conforms geometrically and anatomically with the adjacent vertebral bodies including, but not limited to circular, oval, ellipsoid, annular, kidney-bean, D-shaped, C-shaped, etc. As shown, disc 100 includes an upper endplate 102, a lower endplate 104, and an intermediate elastic membrane 106, the elastic membrane 106 in combination with the upper and lower endplates 102, 104 defining an interior volume 108. The endplates 102, 104 and elastic membrane 106 are similar to those endplates and elastic membrane described previously in relation to other embodiments. The disc 100 may also include a valve (not shown), the valve providing access to the interior 108 of the disc 100 for permitting the insertion of, or removal of, a fluid as previously described in relations to other embodiments. Disc 100 may also include migration resistant features, permanent fixation means and/or implant instrumentation attachment, guiding, and retaining structures as previously described in relation to FIGS. 3a-3e and previous embodiments.

Disc 100 further may include a leaf spring 110 having a first end 112 and second end 114. The first end 112 may be attached to the upper endplate 102, while the second end 114 of leaf spring 110 may comprise a roller 130 capable of rolling on the inner surface of the upper end plate 102. The leaf spring may have a central portion 116 disposed between the first and second end 112, 114, and this central portion 116 may comprise a concavo-convex shape. The convex surface may generally face the lower endplate 24 and the concave surface generally facing the upper endplate 24. Lower end plate 104 may comprise a surface configured to accept intermediate section 116 which itself is configured to mate, articulate, slide and pivot with the inner surface like a ball in a socket. While the leaf spring 110 is described herein as attached to the upper endplate, it may alternatively be attached to the lower endplate 104 so that its concavo-convex intermediate section 116 interacts with the inner surface of the upper end plate 102. It is noted that although the articulating surface of leaf spring 110 is illustrated as being disposed near the center of the leaf spring, the articulating surface may be located at any point along the length and/or width of the leaf spring, as appropriate to provide the desired articulation.

The second unattached end 114 of leaf spring 110 may be provided with a roller 130 on an axle 132, the roller 130 being freely rotatable about the axle 132. The second end 114 of leaf spring 110 may slide or roll along the inner surface of the upper endplate 102 during axial loading or compression and during axial unloading or tension. The leaf spring of this embodiment is thus allowed to translate as it is flexed, providing a greater range of flexibility compared to leaf springs constrained at both ends. In an alternative embodiment, the leaf spring 110 may have a rounded end instead of a roller 130 for sliding directly along the inner surface of the upper endplate 102.

The lower endplate 104 may comprise a pocket 106 for receiving a pad 120. The pad 120 may have a lower surface for engaging the lower endplate 104, and an upper surface comprising a concave section 122 configured and dimensioned to mate with the enlarged intermediate convex section 116 of leaf spring 110. The type and amount of articulation provided by the spring and pad may be adjusted by controlling the curvature provided on the intermediate section 116 and concave section 122. Where the intermediate section 116 has the same radius as the concave section 122, the disc 100 may provide greater support but more constrained movement. Alternatively, where the concave section 122 has a larger radius of curvature than the intermediate section 116, the disc may provide increased articulation.

The intermediate member 116 and concave section 122 may also take on other contours to achieve the desired articulation. The concave section 122 of the pad 120 may be convex to mate with a concave intermediate section 116. Moreover, while the concave section 122 and intermediate member 116 are shown with contours that generally permit mating of their surfaces, non-mating contours may be provided to achieve the desired articulation.

Furthermore, the compression and sliding of leaf spring 110 may vary depending on the area or areas of loading. For example, loading one end of disc 100 may result in greater compression of disc 100 when compared with an opposing end of disc 100. Additionally, the pad 120 and the pocket 106 may be configured to allow the pad to translate within the pocket 106. The varying movements, i.e. compression, of leaf spring 110 and translation of leaf spring 110 with respect to the pocket 106 may allow a moving instantaneous axis of rotation.

Leaf spring 110 may be formed from any appropriate material known in the art including, for example, polymers, ceramics, composites and metals, such as cobalt-chromium alloys, titanium alloys, stainless steel, shape memory alloys, and amorphous alloys. The pad 120 may likewise be formed of similar materials.

Depending on the location of the spine where the disc 100 is implanted, the disc 100 preferably restores height, natural spinal curve (or sagittal balance), stiffness, offers compression stiffness, and allows a range of motion similar to that described in relation to previous embodiments.

Figure 5:
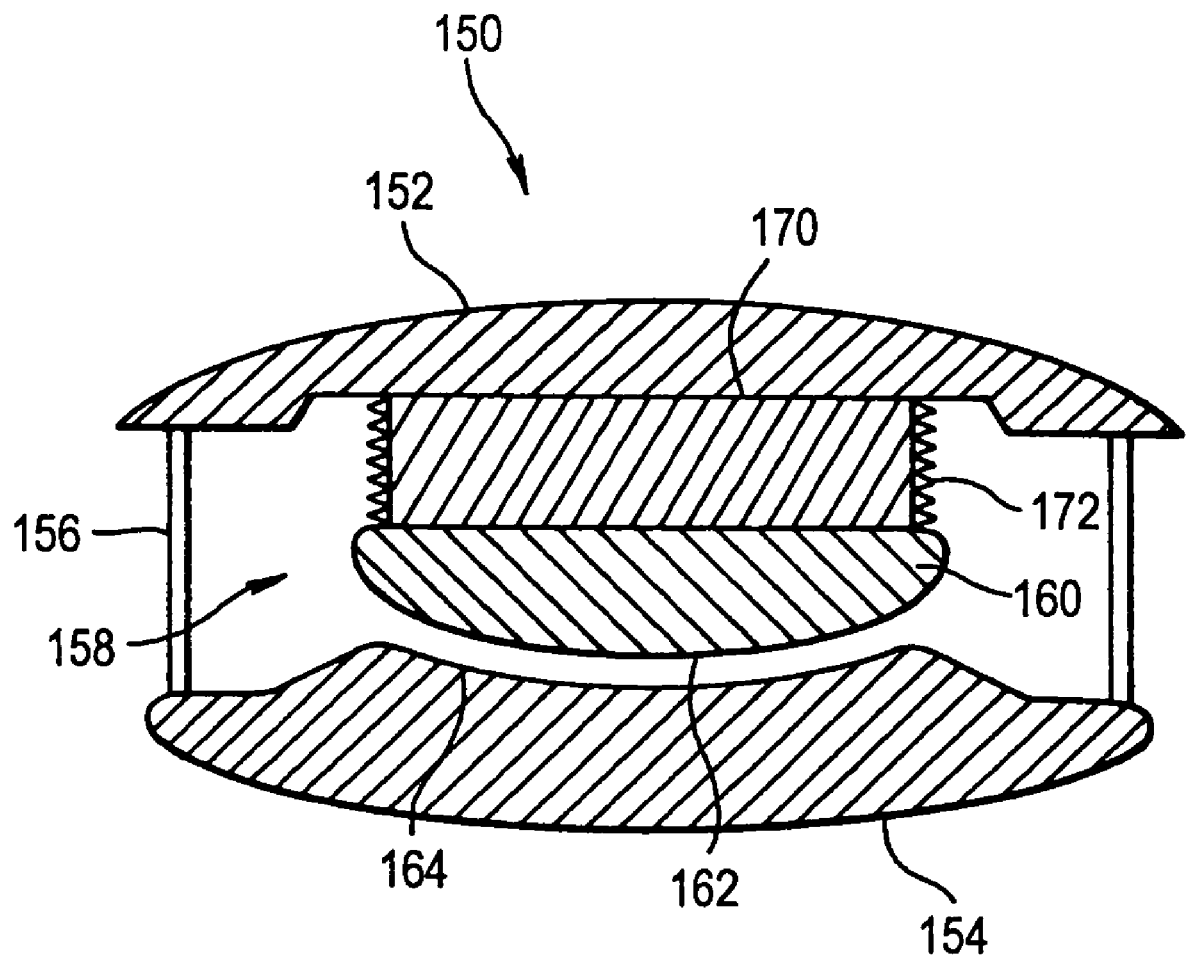
FIG. 5 is a cross-sectional view of a third embodiment of an artificial intervertebral disc according to the present invention.

With reference to FIG. 5, a third exemplary embodiment of an intervertebral disc 150 is shown. Similar to the previous embodiments described, disc 150 may take on any shape that generally conforms geometrically and anatomically with the adjacent vertebral bodies including, but not limited to circular, oval, ellipsoid, annular, kidney-bean, D-shaped, C-shaped, etc. As shown, disc 150 includes an upper endplate 152, a lower endplate 154, and an intermediate elastic membrane 156, the elastic membrane 156 in combination with the upper and lower endplates 152, 154 defining an interior volume 158. The endplates 152, 154 and elastic membrane 156 are similar to those previously described in relation to other embodiments. The disc 150 may also include a valve (not shown), the valve providing access to the interior 158 of the disc 150 for permitting the insertion of, or removal of, a fluid as previously described in relations to other embodiments. Disc 150 may also include migration resistant features, permanent fixation means and/or implant instrumentation attachment, guiding, and retaining structures as previously described in relation to FIGS. 3a-3e and the previous embodiments.

Disc 150 may further include a medial articulating member 160 attached to one of the upper or lower endplates 152, 154, preferably the lower endplate 152. The articulating member 160 may have a convex lower surface 162 that is configured and dimensioned to articulate with respect to concave surface 164 formed on the inner surface of one of the lower endplate 154. The curvature of the corresponding articulating surfaces 162, 164 may be manipulated as necessary to provide the desired amount of articulation and translation between the endplates 152, 154, as has already been described in relation to other embodiments.

Alternatively, the articulating member 162 may comprise a concave lower surface configured and dimensioned to mate and articulate with respect to a convex surface formed on the inner surface of the opposing endplates 152, 154. Furthermore, the concave surface 164 may be integrally formed on the inner surface of one of the endplates 152, 154 or it may be separately formed and mounted thereon. Mounting the concave surface 164 onto the inner surface of one of the endplates 152, 154 permits the concave surface 164 to be made from a material different from that of the associated endplate, for example, polyethylene or other polymer, or a shock absorbing material may be provided, as described in more detail later.

The articulating member 160 may be attached to one of the endplates 152, 154 by any fixation method known in the art including, but not limited to bonding agents, ultrasonic welding, screws, nails, mechanical wedging, and pins. Preferably, however, the articulating member 160 may be attached to one of the endplate 150, 152 via an intermediate shock absorbing layer 170. The shock absorbing layer 170 may be an elastomer, molded or bound polymer fibers, polyurethane, silicone, or any other suitable elastic material having the appropriate shock absorbing properties. Articulating member 160 may be fabricated from a metals, polymers, composites, ceramics, or any combination thereof.

The disc 150 may also include an additional elastic membrane 172 configured to confine and/or secure the articulating member 160 to one of the endplates 152, 154, and/or to encapsulate the shock absorbing layer 170. The additional elastic membrane may be a bellow which may provide shock absorption, compression resistance, and added stability for the articulating member 160 in shear.

Depending on the location of the spine where the disc 150 is implanted, the disc 150 preferably restores height, natural spinal curve (or sagittal balance), stiffness, offers compression stiffness, and allows a range of motion similar to that described in relation to previous embodiments.

As a result of the materials, geometry, and components used, disc 150 can allow flexion/extension, lateral bending, axial rotation, and translation, depending on the loading conditions imparted on the intervertebral disc. In addition, under various spinal loading conditions, the shock-absorbing layer disposed between the articulating member 160 and one of the endplates 152, 154 can compress and/or bend varying amounts, depending on the location of the compressed and/or bent area with respect to the area or areas of loading. Furthermore, disc 150 permits different regions of the disc 150 to compress varying amounts.

Figure 6:
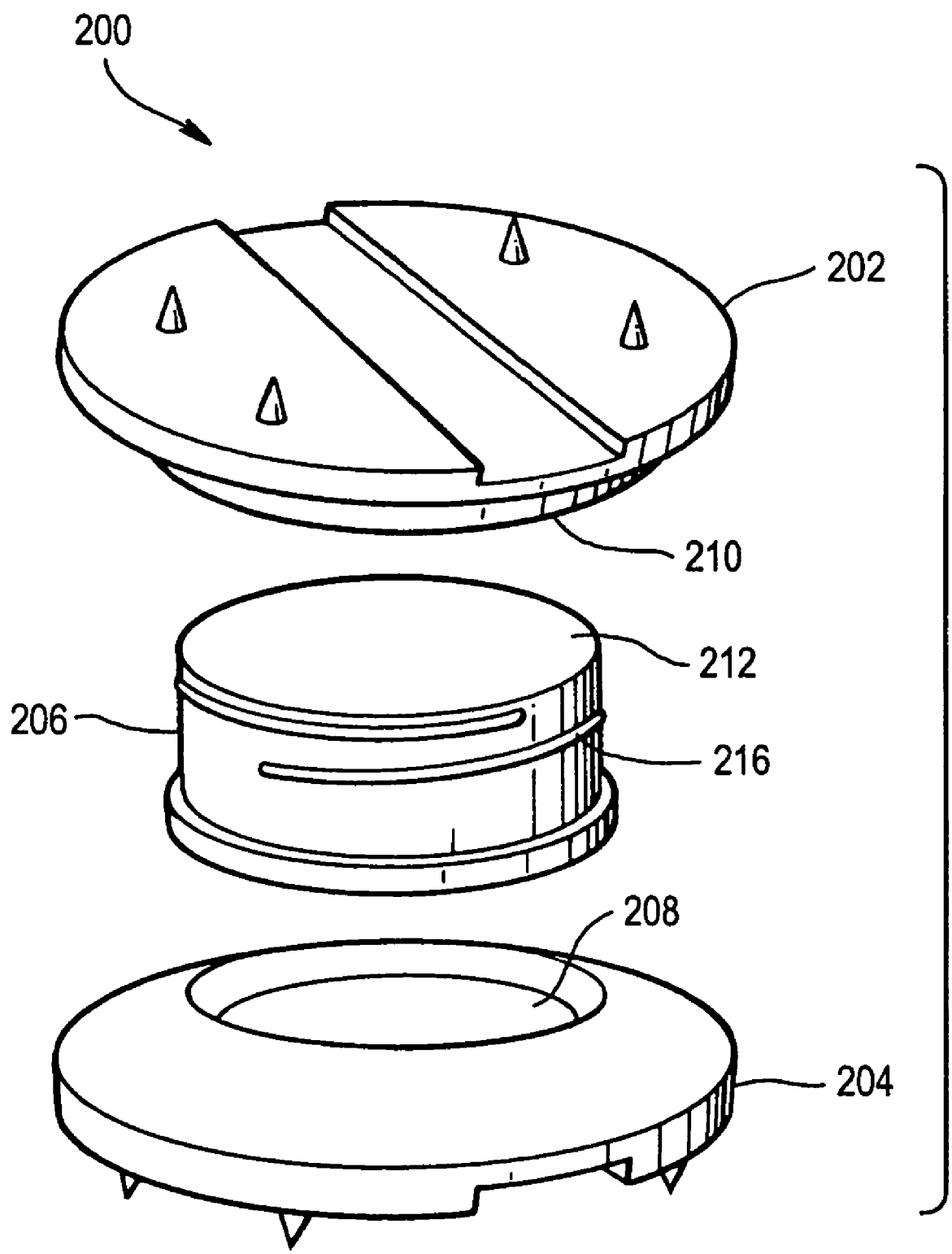
FIG. 6 is a perspective view of a fourth embodiment of an artificial intervertebral disc according to the present invention.

With reference to FIG. 6, a fourth exemplary embodiment of an intervertebral disc 200 is shown. Disc 200 has a generally circular shape with an upper endplate 202, a lower endplate 204, and a slotted core 206 having an upper curved surface and a lower flat surface. The disc 200 may take on any other shape that appropriately conforms geometrically and anatomically with adjacent vertebral bodies, including, but not limited to, kidney-bean shape, oval, annular, ellipsoid, C-shape, D-shape etc. Other features described previously with respect to the other embodiments, such as the migration resistant structures, permanent fixation features and/or implant instrument attachment, guiding, and retaining structures may be included on endplates 202, 204. Furthermore, the outer surfaces of the upper and lower endplates 202, 204 may be substantially flat, wedge-shaped, etc. The outer surfaces of the upper and lower endplates 202, 204 also may be dome shaped with their radii defined in the sagittal and coronal planes to generally match the shape of the ends of the adjacent vertebrae, thereby providing a better fit in situ. Preferably, the upper and lower endplates 202, 204 may be made from metal. However, the upper and lower endplate 202, 204 may alternatively be made from any of the endplate materials previously described in relation to earlier embodiments.

As shown, the lower endplate 204 preferably includes a pocket 208 located on its inner surface, the pocket 208 designed to receive the lower flat surface of slotted core 206. Alternatively, the slotted core 206 and lower endplate 204 may be formed as an integral piece. Where the core is formed as a separate piece, it may comprise a different material from the end plate 204, thus, a metal end plate may be provided having, for example, a polymer mating feature core 206.

Where the core 206 and endplate 204 are formed separately, the disc 200 may also include a c-ring (not shown) or similar structure, such as a lip or ring located within or adjacent to pocket 208, to retain the core 206 within the endplate pocket 208. Such a ring may be configured to prevent the core from translating with respect to the endplate 204, or it may allow translation of the core in one or more directions. Alternatively, the core 206 may be retained in pocket 208 by means such as welding, press-fitting, staking, or bonding a cap (not shown) to the lower endplate 204, the cap covering a portion of the core 206.

Although pocket 208 is shown as having a circular shape, the pocket may take on any other appropriate shape including, but not limited to, oval, elliptical, kidney-bean shaped, rectangular, etc. Where the core and endplate are formed as separate pieces, pocket 208 may be wider or longer than slotted core 206, thus allowing the core 206 to translate within the pocket 208 during operation. Alternatively, the pocket 208 may assume various dimensional configurations necessary to allow translation of the core 206 within the pocket only along specific directions. Thus, the pocket may be provided with a same general width as the core in all directions but one, the pocket being wider than the core in that one direction (e.g. the anterior posterior direction). Thus, a pocket that is wider than the core along the anterior-posterior axis may allow the core to translate in the anterior-posterior direction during use. Corresponding modifications to the pocket geometry may be made to allow translation in other directions, such as medial-lateral translation.

The inner surface of the upper endplate 202 may have a concave mating feature 210 configured to accept the upper curved surface 212 of the slotted core 206. Preferably, the mating feature 210 allows the upper end plate 202 to articulate with respect to the slotted core 206. This mating feature 210 may be integral to the upper end plate 202, or it may be formed as a separate piece, fit to the end plate. Where the mating feature is formed as a separate piece, it may comprise a different material from the end plate 202. Thus, a metal end plate may be provided having, for example, a polymer mating feature 210.

As previously described in relation to other embodiments, the articulating surfaces may be reversed, that is, mating feature 210 may be provided in convex form, and the slotted core may be provided with a concave surface. Furthermore, the type and amount of articulation and/or translation provided by the disc of this embodiment may likewise be adjusted by adjusting the curvature of the convex and concave surfaces as previously described in relation to other embodiments. By allowing articulating and translational movement between the endplates, a moving instantaneous axis of rotation is allowed that approximates the motion of a natural intervertebral disc.

The slotted core 206 may be resilient, allowing it to compress under axial loading, thereby providing shock absorption. Thus the core 206 may have at least one slot 216 cut into its periphery. Slots 216 may be straight or curved and may extend horizontally, vertically, or obliquely. Slots 216 may also vary in length and width and may be provided at various depths through the core. The slots 216 may increase the compressibility of slotted core 206 and thus give additional shock absorbing qualities to the disc 200. The arrangement and configuration of the slots provided in the core 206 may be of any combination appropriate to provide the desired degree of compressibility.

Although shown as having a round footprint, the slotted core 206 may be any other shape including oval, rectangular, elliptical, and kidney-bean. Preferably the shape of the slotted core 206 matches with the shape of the pocket 208 formed on the inner surface of the lower endplate 204. Slotted core 206 may be formed from materials including, for example, ceramics, composites, polymers, or metals such as cobalt-chromium alloys, stainless steel, and titanium alloys. Alternatively, slotted core 206 may be made up of two components (not shown) of differing materials. Also, as previously stated, the slotted core 206 may be made integral with the lower endplate 204.

Disc 200 may also include stiffness restoration features such as an elastic membrane, an elastomer ring, bellow, springs, or fluid as previously discussed in relations to other embodiments. Disc 200 may also incorporate additional shock absorbing features as previously discussed in relations to other embodiments.

The disc 200 endplates may have migration-resistant structures provided on the outer surface of at least one or both of the endplates to impede movement, dislodging, or expulsion of the endplates within and from the ends of the adjacent vertebrae. The migration-resistant structures include, but are not limited to, flaps, spikes, teeth, fins, deployable spikes, deployable teeth, flexible spikes, flexible teeth, alternatively shaped teeth, insertable or expandable fins, screws, hooks, serrations, ribs, and textured surfaces.

Furthermore, the upper and lower endplates of disc 200 also may be coated with a bone growth inducing or conducting substance to promote bony ingrowth to permanently secure the disc to the adjacent vertebrae. Alternatively, the upper and lower endplates may have a roughened surface; a porous surface; laser treated endplate layers; integrate an osteoconductive/osteoinductive scaffold; or may be provided with or made from an integral osteoconductive and/or osteoinductive material to promote bony ingrowth.

Depending on the location of the spine where the disc 200 is implanted, the disc 200 may restore height, lordosis, stiffness, offer compression stiffness, and allow a range of motion intended to mimic that of the natural intervertebral disc, or as required for the particular procedure.

In addition, preferably, as discussed with previous embodiments, the articulating surfaces of disc 200 include a surface polish or similar wear reducing finish such as diamond finish, TiNi finish, etc. in order to minimize wear, decrease particle generation, and increase disc life.

As a result of the materials, geometry, and components used, disc 200 can allow flexion/extension, lateral bending, axial rotation, and translation, depending on the loading conditions imparted on the intervertebral disc. In addition, under various spinal loading conditions, the slotted core 206 can variably compress and allow for different regions of the slotted core 206 to compress in different amounts, depending on the location and type of spinal loading, thus allowing different regions of the endplates 202, 204 to be compressed different amounts. This variable compression of slotted core 206 also allows for a moving instantaneous axis of rotation.

Figure 7:
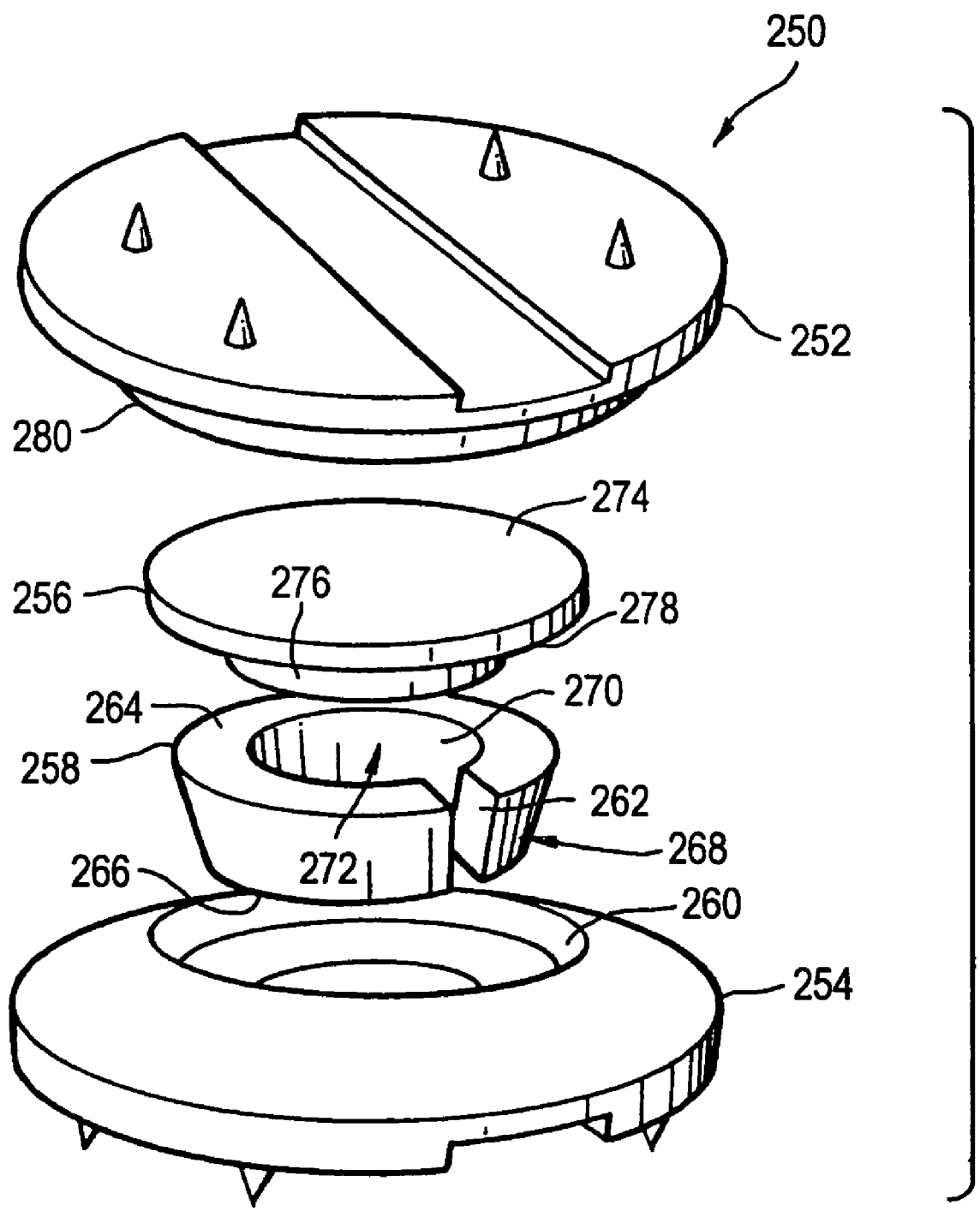
FIG. 7 is a perspective view of a fifth embodiment of an artificial intervertebral disc according to the present invention.

With reference to FIG. 7, a fifth exemplary embodiment of an intervertebral disc 250 is shown. Disc 250 has a generally circular shape with an upper endplate 252, a lower endplate 254, a cap 256 and a ring spring 258. Disc 250, however, may take on other shapes that preferably conform geometrically and anatomically with adjacent vertebral bodies, including, but not limited to, kidney-bean shape, oval, annular, ellipsoid, C-shape, D-shape etc.

As shown, the lower endplate 254 preferably includes a pocket 260 located on its inner surface, the pocket 260 is designed to receive a ring spring 258 having a tapered outer surface, and a cylindrical inner surface. Preferably, the pocket 260 has a tapered inner surface for mating with the tapered outer surface of the ring spring 258. Although pocket 260 is shown as having a circular or conical shape, the pocket 260 may take on any other shape including, but not limited to oval, elliptical, kidney-bean, or rectangular.

Pocket 260 may be larger in dimension than the ring spring 258 to allow the ring spring 258 to translate within the pocket 260. As with the pocket of the previous embodiment, pocket 260 may be specifically dimensioned to allow limited translation of the ring spring 258 in one direction. By allowing translational movement, a moving instantaneous axis of rotation is created. This moving instantaneous axis of rotation more naturally replicates the motion of a natural intervertebral disc.

The disc 250 may also include a c-ring (not shown) or similar type structure, such as a lip or a ring located within or adjacent to the pocket 260, to retain the ring spring 258 in the pocket 260. Alternatively, the ring spring 258 may be retained in pocket 260 by any means known in the art including, but not limited to, welding, press-fitting, staking, or bonding. As previously stated, the ring spring 258 is maintained in the pocket 260 in a manner permitting the ring spring 258 to translate within pocket 260. In one embodiment, the ring spring and cap may be retained in the pocket 260 by a lid that engages the lower endplate 254 and that covers at least a portion of the ring spring 258 and/or the cap 256.

The ring spring 258 is preferably a spring-like element that compresses under axial loading to provide shock absorption, flex and compression resistance. Although shown as having a general "C" shape with a circular footprint, the ring spring 258 may be any other shape including oval, rectangular, elliptical, and kidney-bean. Preferably the shape of the ring spring 258 matches with the shape of the pocket 260 formed on the inner surface of the lower endplate 254. The ring spring 258 may be formed of any appropriate material known in the art including, for example, ceramics, composites, polymers or metals, such as cobalt-chromium alloys, stainless steel and titanium alloys.

As shown, the ring spring 258 has a top surface 264, a bottom surface 266, an outer surface 268 and an inner surface 270 defining a central bore 272 for mating with a shank 276 formed on the cap 256. Preferably, the outer surface 268 of the ring spring 258 is tapered to mate and engage with the inner surface of the pocket 260. In addition, the ring spring 258 may include at least one slot 262 formed and/or cut into its periphery. The slot 262 may be straight or curved and may extend horizontally, vertically, or obliquely. The slot 262 may also vary in length and width. Preferably, as shown, the ring spring 258 includes one vertical slot 262 extending from the top surface 264 the bottom surface 266 of the ring spring 258, and extending from the outer surface 268 to the inner surface 270 of the ring spring 258. The inclusion of this slot 262 increases the compressibility of the ring spring 258 and thus provides additional shock absorbing qualities to the disc 250.

In an alternative embodiment, the ring spring 258 may incorporate a plurality of slots 262 (not shown) running from the top and/or bottom surfaces 264, 266 part way through the thickness of the ring spring 258 to provide desired compressive characteristics of the disc.

The disc 250 may also include a cap 256 having an enlarged body section 274 and a shank 276. The juncture between the enlarged body section 274 and the shank 276 may form a shoulder 278, the shank 276 e configured and dimensioned to be received within the central bore 272 of the ring spring 258, and the shoulder configured to engage the top surface 264 of the ring spring so that the cap 256 may sit on top of the ring spring 258 when the two pieces are assembled. In one embodiment, the central bore 272 is larger than the shank 276 thus permitting compression of the ring spring 258 via closure of the gap created by the at least one slot 262 when a compressive force is placed on the disc 250. Also, providing a central bore 272 which is larger than the shank 276 may permit the cap 256 to translate with respect to the ring spring 258.

As previously described, the shoulder 278 of cap 256 contacts the top surface 264 of the ring spring 258. Thus, axial loads applied to the cap 256 may be transmitted directly to the ring spring 258, pressing it down into the pocket 260. As the ring spring 258 is pressed into the pocket 260, the tapered outside surface 268 of the ring spring 710 engages the tapered surface of the pocket 260, in the process compressing the at least one slots 262. This elastic compression of ring spring 258 under axial loading provides the desired shock absorption and compression resistance. The size of and number of slots provided in the ring spring may be selected as appropriate to provide the desired compressive characteristics of the disc.

The axial displacement of the ring spring 258 may be limited by decreasing the depth of the pocket 260, by decreasing the width of the slot 262, by increasing the thickness and/or length of the shank 276, or by a combination of any or all of these options. Alternatively, a coil spring or elastic layer (both not shown) may be supplied in the pocket 260 to provide an upward bias to the ring spring 258.

The disc 250, as previously stated, also includes an upper endplate 252. Preferably, the inner surface of the upper endplate 252 includes a mating surface 280 which is dimensioned and configured to mate with the top surface of the enlarged body section 274 of the cap 256. Preferably, the mating surface 280 on the upper endplate 252 has a concave surface configured to articulate with a convex surface formed on the top surface of the cap 256. Alternatively, the mating surface 280 may comprise a convex surface and the top surface of the cap 256 may be concave. As previously described in relation to other embodiments, the degree of curvature may be adjusted for either or both surfaces in order to provide the desired articulation and/or translation between the upper endplate and the cap 256.

In an alternative embodiment, the mating surface 280 is provided as a separate piece from the upper endplate 252. The mating surface 280 in such a case may comprise a material different from that of the endplate 252 (for example, the end plate may be titanium while the mating surface may be a UHMWPE). The articulating surfaces of disc 250 may also include a surface polish or similar wear reducing finish such as diamond finish, TiNi finish, etc. in order to minimize wear, decrease particle generation, and increase disc life.

In an alternative embodiment, the separate cap 256 may be eliminated, and the ring spring 256 may incorporate a convex upper surface 264 configured to articulate within the mating surface 280 of the upper endplate 252.

The disc 250 of this embodiment may comprise the additional features described previously with respect to the other embodiments, such as migration resistant structures, permanent fixation features such as porous surfaces or coated surfaces, and/or implant instrument attachment, guiding, and retaining structures may be included on endplates 252, 254. Furthermore, the outer surfaces of the upper and lower endplates 252, 254 may be substantially flat, wedge-shaped, etc. The outer surfaces of the upper and lower endplates 252, 254 may also be dome shaped with their radii defined in the sagittal and coronal planes to generally match the shape of the ends of the adjacent vertebral, thereby providing a better fit in situ. The outer surfaces may further comprise at least one groove, slot, or other features appropriate to allow the disc to be engaged by an insertion instrument. Preferably, the upper and lower endplates 252, 254 are made from metal. However, the upper and lower endplate 252, 254 may alternatively be made from other materials as previously described.

Disc 250 may also include stiffness restoration features such as an elastic membrane, an elastomer ring, bellow, springs, or fluid as previously discussed in relations to other embodiments. Disc 250 may also incorporate any of the shock absorbing features previously discussed in relations to other embodiments.

Depending on the location of the spine where the disc 250 is implanted, the disc 250 preferably restores height, lordosis, stiffness, offers compression stiffness, and allows a range of motion similar to that described in relation to previous embodiments.

As a result of the materials, geometry, and components used, disc 250 can allow flexion/extension, lateral bending, axial rotation, and translation, depending on the loading conditions. In addition under various spinal loading conditions the ring spring 258 can compress varying amounts. This varying compression of ring spring 258 allows for a moving instantaneous axis of rotation. In addition, the ring spring 258 permits different regions of the disc 250 to compress varying amounts.

Figure 8:
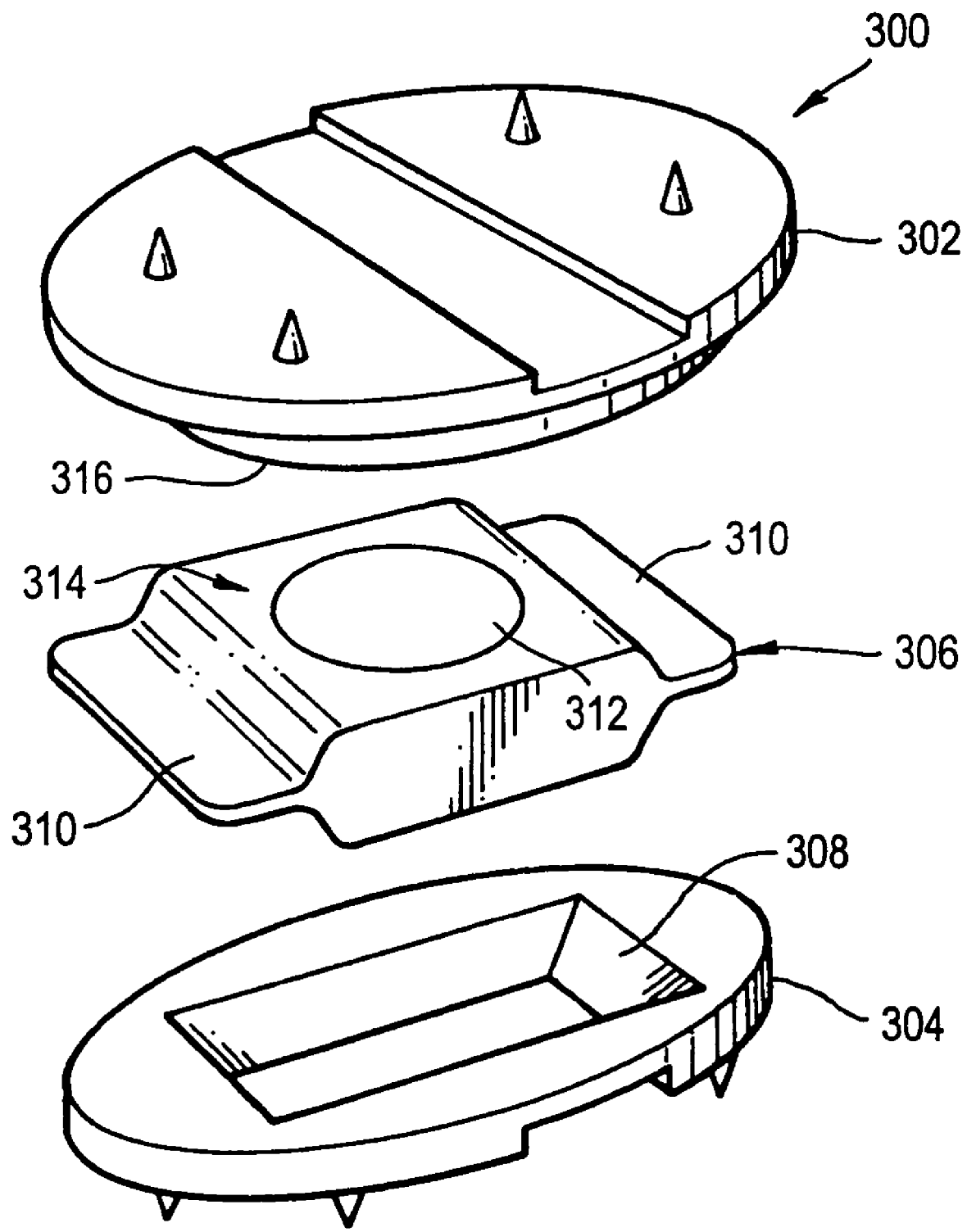
FIG. 8 is a perspective view of a sixth embodiment of an artificial intervertebral disc according to the present invention.

With reference to FIG. 8, a sixth exemplary embodiment of an intervertebral disc 300 is shown. Disc 300 has a generally circular shape with an upper endplate 302, a lower endplate 304, and a winged leaf spring 306 having lateral ends 310. The disc 300, however, may take on other shapes that preferably conform geometrically and anatomically with adjacent vertebral bodies, including, but not limited to, kidney-bean shape, oval, annular, ellipsoid, C-shape, D-shape etc. Other features described previously with respect to the other embodiments, such as migration resistant structures, permanent fixation features and/or implant instrument attachment, guiding, and retaining structures may also be included on the outer surfaces of endplates 302, 304. Furthermore, the outer surfaces of the endplates 302, 304 may be substantially flat, wedge-shaped, etc. The outer surfaces of the upper and lower endplates 302, 304 may also be dome shaped with their radii defined in the sagittal and coronal planes to generally match the shape of the ends of the adjacent vertebral, thereby providing a better fit in situ. Preferably, the upper and lower endplates 302, 304 are made from metal. However, the upper and lower endplate 302, 304 may alternatively be made from other materials as already described.

As shown, the lower endplate 304 preferably includes a cut-out 308 (i.e., a pocket) on its inner surface, the cut-out 308 configured to receive at least a center portion of winged leaf spring 306. The lower endplate 304 may support the winged leaf spring 306 along at least a portion of its lateral ends 310, and the center portion 314 of the leaf spring 306 sits within the cut-out 308, there being a gap between the bottom surface of the leaf spring 306 and the bottom surface of the cut-out 308. Thus, when the leaf spring is subjected to an axial compressive load, the lateral ends 110 may flex, allowing the center portion 314 of the leaf spring to be pressed down into the cut-out 308 until the bottom surface of the center portion contacts the bottom surface of the cut-out 308. The size of the initial gap between the leaf spring and the cutout may be selected, along with the stiffness of the lateral ends 310, to achieve a desired compressive stiffness, as well as a maximum axial compression, of the disc 300. The lateral ends may have stiffnesses that are substantially equivalent, or their stiffnesses may be substantially different. Likewise, the bottom of the cut-out 308 may be substantially flat, or it may be angled to allow greater deflection of the center portion of the leaf spring in a desired direction. The stiffnesses and gaps may be selected as appropriate to mimic the properties of the patient's normal intervertebral disc, or as appropriate for the particular procedure.

Further, the depth of the cut-out 308 may be preferably deep enough to allow the winged leaf spring 306 to flex, however, it is more preferable that the depth of the cut-out 308 is not so deep as to prevent failure of the flexing portions of the winged leaf spring 306 as flexing of the winged leaf spring 306 provides shock absorption and compression resistance which is preferably designed in disc 300 to mimic the compression resistance and shock absorption characteristics of the natural intervertebral disc, or that provides the compression resistance appropriate to the particular procedure.

Although cut-out 308 is shown as having a rectangular shape, the cut-out 308 may take on any other shape including, but not limited to circular, oval, elliptical, kidney-bean, or rectangular. The cut-out 308 may be larger in dimension than the central body portion 314 of winged leaf spring 306 thus allowing for translational movement of the winged leaf spring 306 within the cut-out. By allowing translational movement, a moving instantaneous axis of rotation is created which more naturally replicates the motion of a natural intervertebral disc.

The disc 300 may include an upper endplate 302 having in inner surface comprising a mating surface 316 which is dimensioned and configured to mate with the articulating surface 312 on the central body 314 of the winged leaf spring 306. Preferably, the mating surface 316 is concave. Alternatively, however, the mating surface may have a convex profile, and the mating surface 316 of the upper endplate 302 may be convex and the articulating surface 312 of the central body 314 may be concave. As discussed previously in relation to other embodiments, the degree of curvature of the concave/convex surfaces may be selected to provide the desired amount of articulation to mimic the properties of the normal intervertebral disc, or may be as required for the particular procedure.

In an alternative embodiment the lateral ends 310 of the winged leaf spring 306 may have a constant thickness, length and width. Alternatively, the lateral ends 310 may have a variable thickness, length, and/or width. The transition from the lateral ends 310 to the central body 314 may be gradual such that the thickness gradually increases from the outer periphery of the lateral edge 310 toward the articulating surface 312 or it may be fairly abrupt. In addition, the winged leaf spring 306 may include one or more slots or grooves in either the lateral ends (not shown) to further increase the spring's flexibility.

Although shown as having a rectangular shape, the winged leaf spring 306 may be any other shape including oval, circular, elliptical, kidney-bean, etc. Preferably the shape of the winged leaf spring 306 matches with the shape of the cut-out 308 formed on the inner surface of the lower endplate 304. The winged leaf spring 306 is preferably formed from materials including, for example, ceramics, composites, polymers or metals, such as cobalt-chromium alloys, stainless steel and titanium alloys.

Alternatively, the disc 300, may include a lid or ring member (not shown), configured to retain the winged leaf spring 306 in the cutout 308, thus preventing the spring 306 from dislodging. In this instance, the lid or ring member may be attached to the lower endplate 304 after the winged leaf spring 306 is placed within the cut-out 308. The lid or ring member may be attached to the lower endplate 304 by any fixation means known in the art including, but not limited to pins, screws, welding, bonding, press-fit, etc.

Disc 300 may also include stiffness restoration features such as an elastic membrane, an elastomer ring, bellow, springs, or fluid as previously discussed in relation to various other embodiments. Disc 300 may also incorporate additional shock absorbing features as previously described in relation to other embodiments, for example, manufacturing portions of the disc from elastomeric material, etc.

In addition, the articulating surfaces of disc 300 may be provided with a surface polish or similar wear reducing finish such as diamond finish, TiNi finish, etc. in order to minimize wear, decrease particle generation, and increase disc life.

Depending on the location of the spine where the disc 300 is implanted, the disc 300 preferably restores height, natural spine curve (or sagittal balance), stiffness, offers compression stiffness, and allows a range of motion similar to that described in relation to previous embodiments.

As a result of the materials, geometry, and components used, disc 300 can allow flexion/extension, lateral bending, axial rotation, and translation, depending on the loading conditions imparted on the intervertebral disc.

Figure 9:
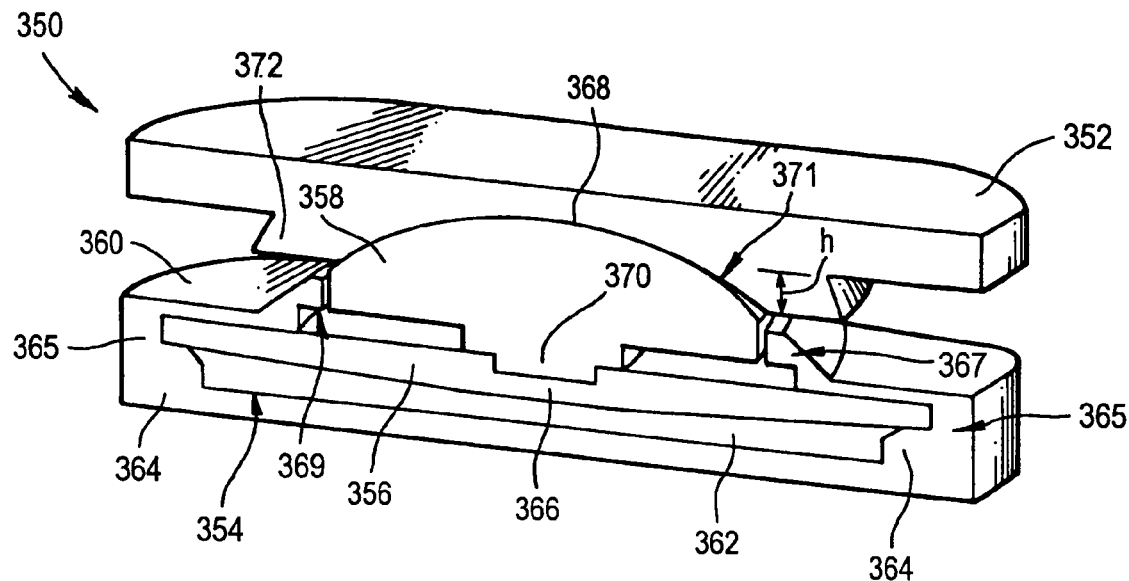
FIG. 9 is a cross sectional view of a seventh embodiment of an artificial intervertebral disc according to the present invention.

With reference to FIG. 9, a seventh exemplary embodiment of an intervertebral disc 350 is shown. Disc 350 has a generally circular shape with an upper endplate 352, a lower endplate 354, a leaf spring 356 and an articulating cap 358. However, the disc 350 may take on other shapes that preferably conform geometrically and anatomically with adjacent vertebral bodies, including, but not limited to, kidney-bean shape, oval, annular, ellipsoid, C-shape, D-shape etc. Other features described previously with respect to other embodiments, such as migration resistant structures, permanent fixation features and/or implant instrument attachment, guiding, and retaining structures may be included on endplates 352, 354. Furthermore, the outer surfaces of the upper and lower endplates 352, 354 may be substantially flat, wedge-shaped, etc. The outer surfaces of the upper and lower endplates 352, 34 may also be dome shaped with their radii defined in the sagittal and coronal planes to generally match the shape of the ends of the adjacent vertebra, thereby providing a better fit in situ. Preferably, the upper and lower endplates 352, 354 are made from metal. However, the upper and lower endplate 352, 354 may alternatively be made from other materials as previously described.

As shown, the lower endplate 354 may comprise a first recess 362 defined by a pair of first shoulder members 364. These shoulder members 364 are configured to support leaf spring 356 along a bottom surface of the leaf spring near its outer perimeter, creating an axial gap between the leaf spring 356 and the recess 362. Thus, when an axial load is applied to the top surface of the leaf spring, it may flex toward and into the recess. The pair of first shoulder members 364 may be integrally formed with the lower endplate 354 or they may comprise separate pieces.

The lower endplate 354 further may have a pair of second shoulder members 365 located axially above and radially outward from the first shoulder members 364. The second shoulder members 365 are configured to engage the perimeter edge of the leaf spring 356, to retain the spring laterally (i.e. translationally) to ensure that the leaf spring remains centered with respect to the first shoulder members 364 and the recess 362, thus assuring appropriate spring flexion. The second shoulder members 365 may be configured to restrain the leaf spring so as to prevent all translational movement. Alternatively, however, the second shoulder members 365 may be laterally offset from the leaf spring in at least one direction, thus allowing the leaf spring to translate in the at least one direction. By allowing such translational movement, a moving instantaneous axis of rotation is created, which more naturally replicates the motion of a natural intervertebral disc.

A cover plate 360 may be provided to cover the leaf spring, preventing the leaf spring from moving axially out of engagement with the pairs of first and second shoulder members 364. In this embodiment, the cover plate 360 may be attached to the top surface of the pair of second shoulder members 365. The cover plate 360 may be attached to the second shoulder members 365 by any fixation means known in the art including, but not limited to press-fit, welding, pins, screws, bonding, etc. The cover plate 360 may have an outer perimeter sized to approximate the outer perimeter of the lower endplate 354, and an inner opening 369 sized to accept an articulation element (to be discussed in more detail below). The cover plate 360 inner opening may include an upwardly extending inner edge 367 that may act in combination with a corresponding surface on the upper endplate 352 to limit articulation of the disc 350. The cover plate may also be configured to accept a disc insertion instrument. The embodiment of FIG. 9 illustrates the leaf spring 356 as a separate element from the lower endplate 354, however, in an alternative embodiment shown in FIG. 9a, the leaf spring 356 may be integrally formed with the lower endplate 354.

The leaf spring 356 may be a spring-like element that flexes under axial loading to provide shock absorption, flexion and compression resistance. The leaf spring 356 may have a uniform thickness, or its thickness may vary. In the embodiment illustrated in FIG. 9, the leaf spring has a greater thickness in the center than at its ends; in the embodiment illustrated in FIG. 9a, the leaf spring is thicker at the center and the ends, and has thinner segments between the ends and the center, rendering the leaf spring with a waved shape when viewed in cross section. The leaf spring may have any thickness appropriate to provide the required shock absorption, flexion and compression resistance.

The leaf spring 356 may be formed from any appropriate material known in the art, including, for example, ceramics, composites, polymers, or metals such as cobalt-chromium alloys, stainless steel and titanium alloys.

Articulating cap 358 may be provided with a convex upper articulation surface 368 and with a lower, leaf spring-engaging, protrusion 370. The articulation surface 368 may be configured to mate and articulate with a mating surface 371 formed on the inner surface of the upper endplate 352. The mating surface 371 may comprise a concave surface corresponding to the convex surface of the articulating cap 358. Alternatively, the upper endplate mating surface 371 may be convex and the top surface of the articulating cap 358 may be concave. The curvatures of the respective articulation surface 368 and mating surface 371 may be selected to provide the appropriate type and amount of articulation and/or translation to mimic the movement of the patient's natural disc, or as required for the particular procedure.

Figure 9A:
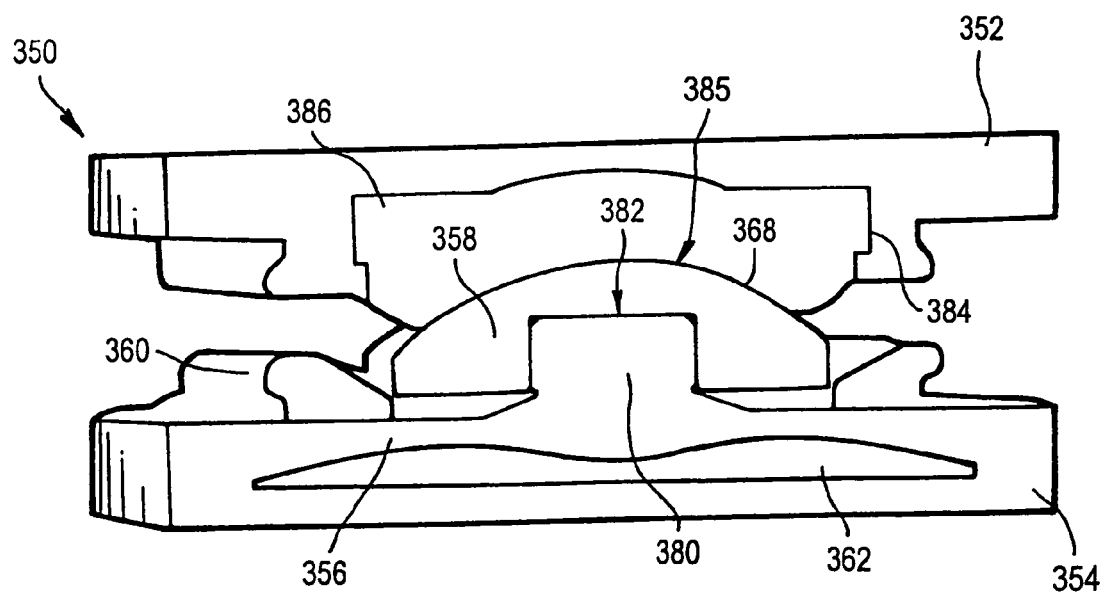
FIG. 9a is an alternate cross-sectional view of the seventh embodiment of an artificial intervertebral disc according to the present invention.

The mating surface 371 of the upper endplate 352 may be integral with the endplate, or as illustrated in FIG. 9a it may be formed as a separate piece and attached to the endplate using any appropriate fixation method known in the art, and as previously described for other embodiments. When formed as a separate piece, the mating surface 371 may comprise a material different from that of the endplate, such as the various materials described as appropriate for articulation surfaces in relation to other embodiments. The mating surface 371 may be recessed into a raised portion 372 of endplate 352, which may allow the endplate 352 to be relatively thin without limiting the radius of curvature that may be provided for the concave mating surface 371 and/or requiring the mating surface to be too shallow.

The raised portion 372 of the upper endplate 352 may comprise a raised face 374 having a raised face height "h."

The raised face 374 may be configured to engage the upwardly extending inner edge 367 of the leaf spring cover plate 360 to limit articulation of the disc 350 in at least one direction. Alternatively, the raised face 374 and the upwardly extending inner edge 367 may be configured to limit articulation of the disc in all directions. In one embodiment, the raised face 374 and inner edge 367 may be configured to limit articulation of the disc in a single plane only, (e.g. the medial-lateral plane). The raised face 374 and inner edge 367 may comprise any combination of configurations appropriate to provide the disc 350 with the desired range of articulation in all planes. Thus, the raised face 374 height "h" may be different at different locations about the disc, for example, the height "h" may be smaller on the anterior and posterior sides of the disc 350 and greater on the lateral sides of the disc, thus controlling the degree of articulation in the anterior-posterior direction. Alternatively, the raised face 374 and inner edge 367 may comprise mating surfaces, such as flat faces, correspondingly curved surfaces, angled faces, stepped faces, etc., to control the degree of articulation of the disc in the desired direction.

The bottom surface of the articulating cap 358 may further comprise a protrusion 370 which is dimensioned and configured to mate with a groove 366 formed on the upper surface of the leaf spring 356. Thus, the cap 358 may be at least partially restrained within groove 366. In one embodiment, groove 366 may be sized the same or only slightly larger than the protrusion 370, thereby rendering the cap restrained transversely. In an alternative embodiment, the groove may be larger than the protrusion in at least one direction (e.g. along the anterior-posterior axis), thus allowing the cap 358 to move transversely (i.e. translate) in that direction during operation. By allowing translational movement, a moving instantaneous axis of rotation is provided. This moving instantaneous axis of rotation may more naturally replicate the motion of a natural intervertebral disc.

Alternatively, the protrusion 370 may be rigidly secured within the groove 366, thus permitting no translational movement.

It is noted that although the groove and protrusion are illustrated as having substantially corresponding rectangular shapes, the protrusion 370 and groove 366 may take on any other appropriate shape known in the art including, but not limited to circular, oval, ellipsoidal, etc., to provide the requisite translational freedom.

Figure 9B:
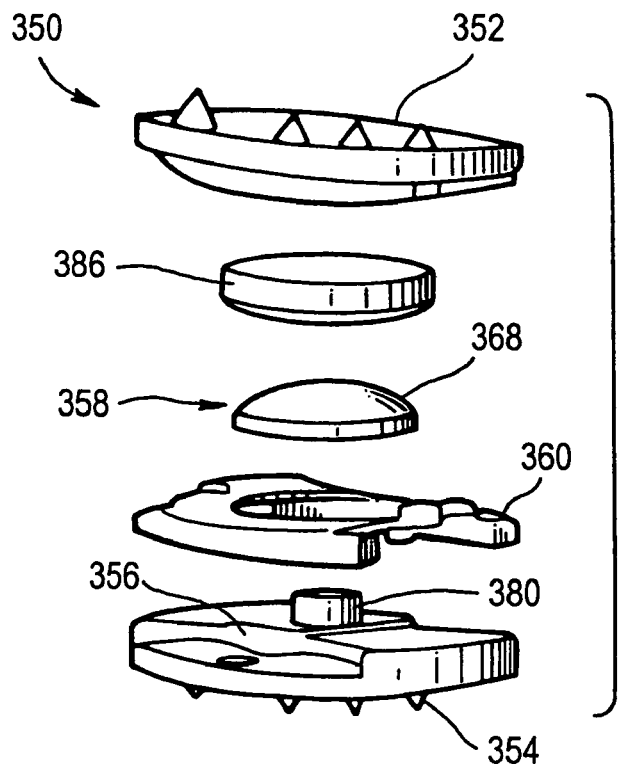
Figure 9C:
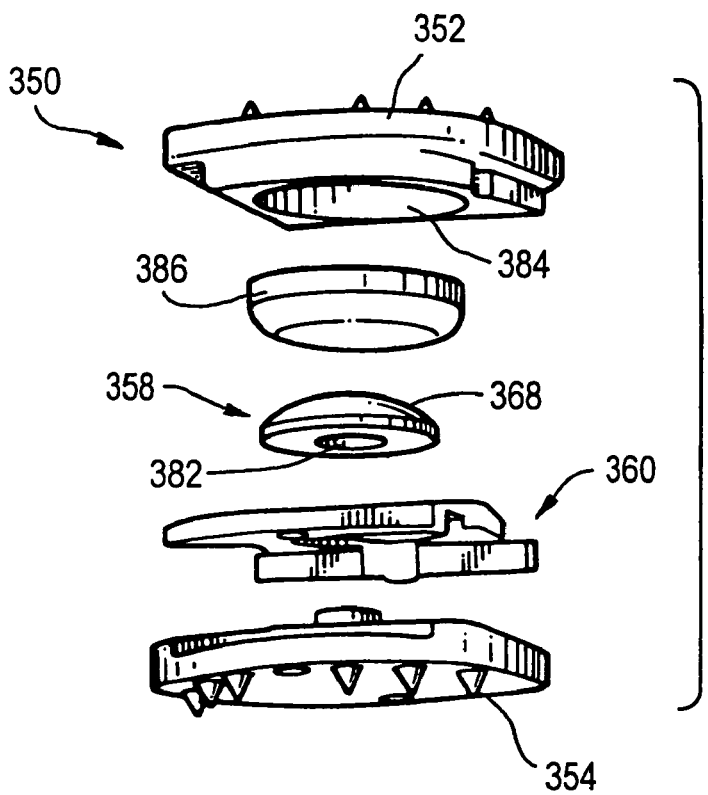

In an alternative embodiment, shown in FIGS. 9a through 9c, the leaf spring 356 may comprise a post 380 and the cap 358 may have a groove 382 for receiving the post 380. The groove 366 and post 380 may be sized and configured to allow translation of the cap 358 with respect to the lower endplate 354 in at least one direction. When the groove 382 and post 380 are configured to allow translation of the cap 358, the cover plate 360 also must be configured so that the translating cap 358 does not interfere with the cover plate center opening 369. Thus, in such a case, the center opening may be elongated or rectangular in the direction of translation.

The upper endplate 352 may include a recess 384 for receiving an articulating insert 386, the insert having a concave surface 385 configured to articulate with the convex articulating surface 368 of the cap 358. As previously described, providing a concave articulating insert 384 may provide the surgeon with greater flexibility in selecting the appropriate material to comprise the articulating surfaces while not affecting the material of the endplates 352, or otherwise affecting the design or installation of the other components of the disc 350. Thus the insert 384 may be formed of any appropriate material known in the art including but not limited to polymers including rigid polymers, such as PEEK or UHMWPE, ceramics, composites or any combinations thereof.

When an articulating insert 386 is provided, the recess 384 in the upper endplate 352 may comprise a surface configured to retain the insert 386. The recess may comprise a radial ridge configured to fit within a corresponding radial groove in the insert such that the insert may be snapped into the recess. Alternatively, the insert may be attached to the recess via a press fit, by using a bonding agent, or any combination thereof.

In an alternative embodiment, disc 350 may also include stiffness restoration features such as an elastic membrane, an elastomer ring, bellow, springs, or fluid as previously discussed in relations to other embodiments. Disc 350 may also incorporate additional shock absorbing features as previously discussed in relations to other embodiments.

In addition, as discussed with previous embodiments, the articulating surfaces of disc 350 may include a surface polish or similar wear reducing finish such as diamond finish, TiNi finish, etc. in order to minimize wear, decrease particle generation, and increase disc life.

The disc 350 endplates may have migration-resistant structures provided on the outer surface of at least one or both of the endplates to impede movement, dislodging, or expulsion of the endplates within and from the ends of the adjacent vertebrae. The migration-resistant structures include, but are not limited to, flaps, spikes, teeth, fins, deployable spikes, deployable teeth, flexible spikes, flexible teeth, alternatively shaped teeth, insertable or expandable fins, screws, hooks, serrations, ribs, and textured surfaces.

Furthermore, the upper and lower endplates of disc 350 also may be coated with a bone growth inducing or conducting substance to promote bony ingrowth to permanently secure the disc to the adjacent vertebrae. Alternatively, the upper and lower endplates may have a roughened surface; a porous surface; laser treated endplate layers; integrate an osteoconductive/osteoinductive scaffold; or may be provided with or made from an integral osteoconductive and/or osteoinductive material to promote bony ingrowth.

Depending on the location of the spine where the disc 350 is implanted, the disc 350 may restore height, lordosis, stiffness, offer compression stiffness, and allow a range of motion intended to mimic that of the natural intervertebral disc, or as required for the particular procedure.

As a result of the materials, geometry, and components used, disc 350 can allow flexion/extension, lateral bending, axial rotation, and translation, depending on the loading conditions imparted on the intervertebral disc.

Figure 10:
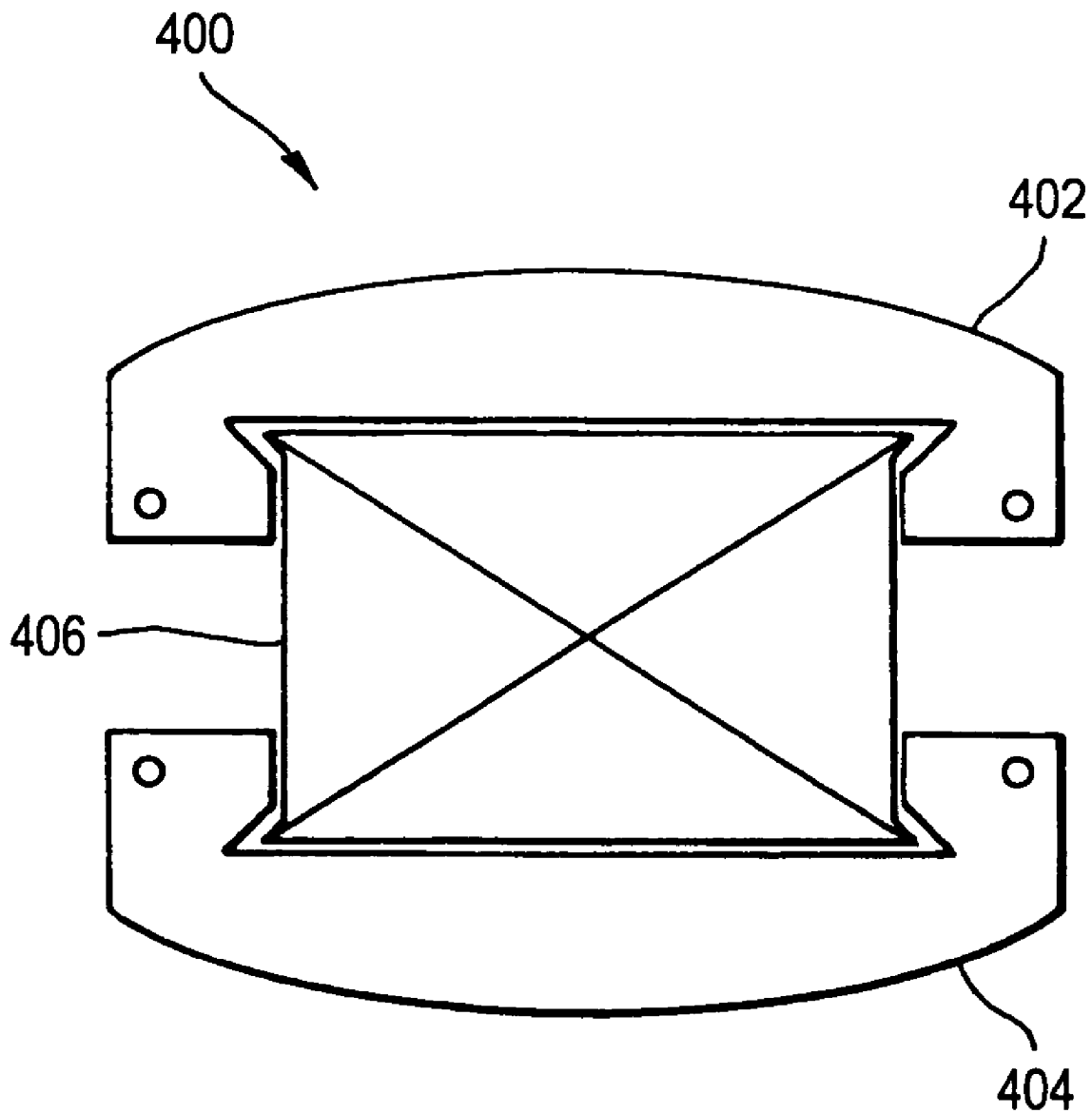
FIG. 10 is schematic view of a eight embodiment of an intervertebral disc according to the present invention.

With reference to FIG. 10, an exemplary installation procedure will be described. Generally speaking the disc 400 may include an upper endplate 402, a lower endplate 404 and a core mechanism 406, the core mechanism being any spring, slotted core, ring spring, leaf spring, coil spring, elastomer, fluid filled or articulating disc previously described herein. The intervertebral disc 400 may be implanted in a modular fashion, for example, the endplates 402, 404 of disc 400 may be inserted into the intervertebral cavity using instruments such as a distractor and/or holder instrument. The intervertebral disc space may then be distracted using a standard spinal distractor which engages the endplates 402, 404. Trial spacers may then be used to determine the appropriate size of the core mechanism 406 to be inserted in the resulting disc space. In an exemplary embodiment, the core mechanism, 406 is inserted and attached to endplates 402, 404 through the use of a dovetail, slot, or similar connection. This modular insertion technique may avoid over-distracting the intervertebral space, which may damage surrounding tissue and/or blood vessels.

Alternatively, the intervertebral disc 400 may be inserted preassembled with the use of particular insertion tools. For example, an endplate holding clip may be used that allows the endplates 402, 404 to be held and locked in a parallel and spaced relationship as they are inserted into the intervertebral space. Once implanted, the clip may be unlocked and removed from the endplates 402, 404. The clip may then be removed from the intervertebral space. In addition, the disc 400 may be implanted in a compressed state to prevent over-distraction. The introduction of the disc 400 in a compressed state may be accomplished via a surgical insertion instrument or by an internal mechanism located in the disc 400.

An anterior, lateral, or anterolateral surgical approach may be used for the intervertebral disc 400. Furthermore, depending on the intervertebral disc 400 to be implanted, a minimally invasive surgical method or a simultaneous distraction and implantation surgical method may be used. Simultaneous distraction and implantation may be accomplished, for example, by using slots formed on the outer surface of the endplates 402, 404 to guide the implant down the distractor during implantation. Also, depending on the intervertebral disc to be implanted, an artificial Anterior Longitudinal Ligament or the natural Anterior Longitudinal Ligament may be attached directly to the disc or to the adjacent vertebral bodies. Attachment of the Anterior Longitudinal Ligament may assist in preventing movement, dislodging or expulsion of the implant. To assist with the implantation of the intervertebral discs, the intervertebral discs may include alignment markers.

While various descriptions of the present invention are described above, it should be understood that the various features can be used singly or in combination thereof. Therefore, this invention is not to be limited to the specific preferred embodiments depicted herein.

Further, it should be understood that variations and modifications within the spirit and scope of the invention may occur to those skilled in the art to which the invention pertains. For example, some portions of the implants disclosed herein may be formed of bone, such as allografts, autografts, and xenografts, which may be partially or fully demineralized. In addition, some implants may include bone material or other bone growth inducing material in their interiors or on/in their endplates. Such substances in the interiors may be permitted to interact with the surrounding anatomy, as with channels or other holes formed in the implant walls. Also, intra and post-operative alignment markers may be used to assist with implantation of the intervertebral discs. Furthermore, the intervertebral discs can be made rigid in situations where fusion is necessary. The intervertebral discs may be made rigid by, for example, allowing fusion between the endplates, inserting spacers between the endplates, or by injecting a solidifying liquid between the endplates. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. An articulating intervertebral implant for implantation between first and second vertebrae, the implant comprising:
    a first endplate having a first inner surface and a first outer surface for engaging the first vertebra;
    a second endplate having a second inner surface and a second outer surface for engaging the second vertebra;
    a cover plate coupled to the first endplate, the cover plate including an inner opening;
    a first insert member adapted to be received within the inner opening of the cover plate, the first insert member having a first articulating surface operatively associated with the second endplate so that the first and second endplates can articulate with respect to each other; and
    a spring component located between the first insert member and the first endplate, wherein the spring component is a leaf spring.

2. The articulating implant of claim 1, wherein the leaf spring has first and second resilient ends configured to engage the first endplate, and a length.

3. The articulating implant of claim 2, wherein the first endplate further comprises a recess having a length smaller than the length of the leaf spring so that when the leaf spring engages the first endplate, the first and second resilient ends are supported on the inner surface of the first endplate.

4. The articulating implant of claim 3, wherein the leaf spring further comprises a central portion, the central portion of the leaf spring being axially spaced from the first inner surface of the first endplate.

5. The articulating implant of claim 4, wherein the first endplate and leaf spring are configured so that the leaf spring can translate in at least one direction with respect to the first endplate.

6. The articulating implant of claim 1, wherein the first endplate further comprises a pair of first shoulder members for supporting the leaf spring on either end thereof so that a bottom surface of the leaf spring is axially spaced from the first inner surface of the first endplate.

7. The articulating implant of claim 6, wherein the first endplate further comprises a pair of second shoulder members located axially above and radially outward from the pair of first shoulder members, the second shoulder members contacting a perimeter edge of the leaf spring so that the leaf spring is laterally retained.

8. The articulating implant of claim 7, wherein the pair of second shoulder members is configured to prevent all translational movement of the leaf spring.

9. The articulating implant of claim 7, wherein the pair of second shoulder members is configured to enable the leaf spring to translate in at least one direction.

10. The articulating implant of claim 1, wherein the leaf spring includes a first surface and a second surface, the first surface being associated with the first endplate, the second surface being associated with the first insert member.

11. The articulating implant of claim 10, wherein the first endplate further comprises a recess formed in the first inner surface, the leaf spring having a length sufficient to span the recess so that at least opposite ends of the leaf spring are supported by the first inner surface and a central portion of the leaf spring is positioned over the recess so that the central portion moves into the recess when a compressive force is applied to the second surface of the leaf spring.

12. The articulating implant of claim 10, wherein the first endplate further comprises a perimeter edge configured to allow the leaf spring to translate with respect to the first endplate in at least one direction.

13. The articulating implant of claim 10, wherein the first endplate further comprises a perimeter edge configured to prevent the leaf spring from translating in at least one direction.

14. The articulating implant of claim 1, wherein the leaf spring further comprises a top surface, the top surface of the leaf spring including a recess to accept a projection formed on the first insert member.

15. The articulating implant of claim 14, wherein the recess and projection enable the first insert members to translate in at least one direction relative to the leaf spring.

16. The articulating implant of claim 1, wherein the cover plate engages at least a portion of the first endplate and covers at least a portion of the leaf spring to prevent the leaf spring from axially disengaging from the first endplate.

17. The articulating implant of claim 16, wherein the cover plate farther comprises at least one raised ridge to contact at least one raised ridge associated with the second endplate to limit articulation between the endplates in at least one direction.

18. The articulating implant of claim 17, wherein the raised ridges have corresponding flat surface profiles.

19. The articulating implant of claim 17, wherein the raised ridges have correspondingly angled surfaces.

20. The articulating implant of claim 1, wherein the first and second endplates are formed from a material selected from the group consisting of metal, polymer, ceramic and composite.

21. The articulating implant of claim 1, wherein the first and second endplates are formed of bone material selected from the group consisting of cortical, cancellous, allograft, autograft, xenograft, demineralized and partially demineralized bone.

22. The articulating implant of claim 1, wherein the leaf spring is integral with the first endplate.

23. An articulating intervertebral implant for implantation between first and second vertebrae, the implant comprising:
  a first endplate having a first inner surface and a first outer surface for engaging the first vertebra;
  a second endplate having a second inner surface and a second outer surface for engaging the second vertebra;
  a cover plate coupled to the first endplate, the cover plate including an inner opening;
  a first insert member adapted to be received within the inner opening of the cover plate, the first insert member having a first articulating surface operatively associated with the second endplate so that the first and second endplates can articulate with respect to each other;
  a second insert member located between the second endplate and the first insert member, the second insert member having a second articulating surface for contacting the first articulating surface formed on the first insert member; and
  a spring component located between the first insert member and the first endplate.

24. An articulating intervertebral implant for implantation between first and second vertebrae, the implant comprising:
  a first endplate having a first inner surface and a first outer surface for engaging the first vertebra;
  a second endplate having a second inner surface and a second outer surface for engaging the second vertebra;
  a cover plate coupled to the first endplate, the cover plate including an inner opening;
  a first insert member adapted to be received within the inner opening of the cover plate, the first insert member having a first articulating surface;
  a second insert member located between the second endplate and the first insert member, the second insert member having a second articulating surface for contacting the first articulating surface formed on the first insert member;
  a spring component located between the first insert member and the first endplate so that the first and second endplates can axially move with respect to one another.

25. The articulating implant of claim 24, wherein the spring component is a leaf spring.

26. The articulating implant of claim 25, wherein the leaf spring has first and second resilient ends configured to engage the first endplate, and a length.

27. The articulating implant of claim 26, wherein the first endplate further comprises a recess having a length smaller than the length of the leaf spring so that when the leaf spring engages the first endplate, the first and second resilient ends are supported on the inner surface of the first endplate.

28. The articulating implant of claim 27, wherein the leaf spring farther comprises a central portion, the central portion of the leaf spring being axially spaced from the first inner surface of the first endplate.

29. The articulating implant of claim 28, wherein the first endplate and leaf spring are configured so that the leaf spring can translate in at least one direction with respect to the first endplate.

30. The articulating implant of claim 25, wherein the first endplate further comprises a pair of first shoulder members for supporting the leaf spring on either end thereof so that a bottom surface of the leaf spring is axially spaced from the first inner surface of the first endplate.

31. The articulating implant of claim 30, wherein the first endplate further comprises a pair of second shoulder members located axially above and radially outward from the pair of first shoulder members, the second shoulder members contacting a perimeter edge of the leaf spring so that the leaf spring is laterally retained.

32. The articulating implant of claim 31, wherein the pair of second shoulder members is configured to prevent all translational movement of the leaf spring.

33. The articulating implant of claim 31, wherein the pair of second shoulder members is configured to enable the leaf spring to translate in at least one direction.

34. The articulating implant of claim 25, wherein the leaf spring includes a first surface and a second surface, the first surface being associated with the first endplate, the second surface being associated with the first insert member.

35. The articulating implant of claim 34, wherein the first endplate further comprises a recess formed in the first inner surface, the leaf spring having a length sufficient to span the recess so that at least opposite ends of the leaf spring are supported by the first inner surface and a central portion of the leaf spring is positioned over the recess so that the central portion moves into the recess when a compressive force is applied to the second surface of the leaf spring.

36. The articulating implant of claim 25, wherein the leaf spring further comprises a top surface, the top surface of the leaf spring includes a post and the first insert member includes a groove, the post being receivable in the groove.

37. The articulating implant of claim 36, wherein the post and groove enable the first insert member to translate in at least one direction relative to the leaf spring.

38. The articulating implant of claim 25, wherein the cover plate engages at least a portion of the first endplate and covers at least a portion of the leaf spring to prevent the leaf spring from axially disengaging from the first endplate.

39. The articulating implant of claim 38, wherein the cover plate further comprises at least one raised ridge to contact at least one raised ridge associated with the second endplate to limit articulation between the endplates in at least one direction.

40. The articulating implant of claim 25, wherein the leaf spring is integral with the first endplate.

* * * * *